(12) United States Patent
Mason et al.

(10) Patent No.: US 9,968,473 B2
(45) Date of Patent: May 15, 2018

(54) ORTHOPEDIC BRACE SECURING AND TENSIONING SYSTEM

(71) Applicant: United Surgical Associates, Inc., Solvang, CA (US)

(72) Inventors: Jeffrey T. Mason, Escondido, CA (US); Russell S. Moir, Solvang, CA (US); Bryan K. Bowman, Roann, IN (US)

(73) Assignee: United Surgical Associates, Inc., Solvang, CA (US)

( * ) Notice: Subject to any disclaimer, the term of this patent is extended or adjusted under 35 U.S.C. 154(b) by 562 days.

(21) Appl. No.: 14/446,219

(22) Filed: Jul. 29, 2014

(65) Prior Publication Data

US 2015/0038889 A1     Feb. 5, 2015

Related U.S. Application Data

(60) Provisional application No. 61/860,215, filed on Jul. 30, 2013.

(51) Int. Cl.
| | |
|---|---|
| *A61F 5/00* | (2006.01) |
| *A61F 5/01* | (2006.01) |
| *A43C 11/16* | (2006.01) |
| *A61B 17/132* | (2006.01) |

(52) U.S. Cl.
CPC .......... *A61F 5/0123* (2013.01); *A43C 11/165* (2013.01); *A61B 17/132* (2013.01); *A61F 5/01* (2013.01); *A61F 5/0125* (2013.01); *A61F 2005/0137* (2013.01); *Y10T 24/2191* (2015.01)

(58) Field of Classification Search
CPC ........ A61F 5/0123; A61F 5/0125; A61F 5/00; A61F 5/01; A61F 2005/0132; A61B 17/132; Y10T 24/2191
See application file for complete search history.

(56) References Cited

U.S. PATENT DOCUMENTS

| | | | |
|---|---|---|---|
| 5,159,732 | A | 11/1992 | Burke |
| 5,766,140 | A | 6/1998 | Tillinghast, III |
| 2004/0054311 | A1 | 3/2004 | Sterling |
| 2005/0240135 | A1 | 10/2005 | Hoffmeier et al. |
| 2005/0267518 | A1 | 12/2005 | Wright et al. |
| 2010/0049108 | A1 | 2/2010 | Napholz |
| 2012/0046585 | A1 | 2/2012 | Lee et al. |

(Continued)

FOREIGN PATENT DOCUMENTS

WO     2006078428 A2     7/2006

*Primary Examiner* — Kim M Lewis
(74) *Attorney, Agent, or Firm* — Felix L. Fischer

(57) ABSTRACT

An attachment system for an orthopedic brace incorporates at least one cinching system assembly having a knob rotatable in a first direction and a second direction. At least one cinching plate is engaged by the knob for rotation in the first direction in a first orientation and transitions to a second orientation upon rotation in the second direction. A ratchet wheel is engaged by the cinching plate in the first orientation for rotation in the first direction. At least one ratchet arm engages the ratchet wheel for ratcheting operation and is engaged by the cinching plate in the second orientation for disengagement from the ratchet arm. A shaft is rotated in response to rotation of the ratchet wheel and a strap is extendible from and retractable on the shaft upon rotation of the shaft.

14 Claims, 32 Drawing Sheets

(56) References Cited

U.S. PATENT DOCUMENTS

2012/0271211 A1   10/2012  Bledsoe
2015/0040359 A1*  2/2015  Brown .................. B60P 7/0861
                                                      24/68 CD
2015/0089835 A1*  4/2015  Hammerslag ............ A43B 5/16
                                                        36/83

\* cited by examiner

ORTHOPEDIC BRACE SECURING AND TENSIONING SYSTEM

REFERENCES TO RELATED APPLICATIONS

This application claims the priority of U.S. provisional application Ser. No. 61/860,215 filed on Jul. 30, 2013 entitled ORTHOPEDIC BRACE SECURING AND TENSIONING SYSTEM having a common assignee with the present application, the disclosure of which is incorporated herein.

BACKGROUND INFORMATION

Field

Embodiments of the disclosure relate generally to the field of anatomical support braces and more particularly to a system for securing and tensioning including ratcheting tensioning with optional selectable spring loaded strap retraction, strap quick release and orientation relief for orthopedic braces including knee braces.

Background

While orthopedic braces come in various overall sizes, each brace typically require adjustable straps to fit various anatomically sized users. For knee braces as an example, thigh and calf circumference may vary widely for users of a brace having a common size based on leg length. For most applications users prefer to easily don the brace and quickly adjust the various straps for appropriate size and tension. Having appropriate tension in the straps may be critical for proper operation of the brace. Equally as important is the ability to quickly and easily remove the brace when an activity requiring the brace is complete.

It is therefore desirable to provide a securing system for orthopedic braces which can incorporate rapidly and easily adjustable tensioning and release for securing straps encircling the anatomical element.

SUMMARY

Embodiments disclosed herein provide as a first feature an attachment system for an orthopedic brace which incorporates at least one cinching system assembly having a knob rotatable in a first direction and a second direction. At least one cinching plate is engaged by the knob for rotation in the first direction in a first orientation and transitions to a second orientation upon rotation in the second direction. A ratchet wheel is engaged by the cinching plate in the first orientation for rotation in the first direction. At least one ratchet arm engages the ratchet wheel for ratcheting operation and is engaged by the cinching plate in the second orientation for disengagement from the ratchet arm. A shaft is rotated in response to rotation of the ratchet wheel and a strap is extendible from and retractable on the shaft upon rotation of the shaft.

Embodiments herein also provide as a feature a tensioning assembly for orthopedic braces which incorporates a knob having a spindle with an attached ratchet. A spool is engaged for rotation by the spindle. A floating arm has a first position and a second position. The floating arm includes a locking tooth extendible into a connection channel in the second position, a ratchet release loop positioning a ratchet lock for engagement of the ratchet in the second position and a release button for moving the floating arm from the second position to the first position. A strap has a bullnose removably receivable in the connection channel. The bullnose has a slot to receive the locking tooth and releases the floating arm from the first position to said second position upon insertion into the connection channel. The strap is extendible from and retractable on the spool.

The features, functions, and advantages that have been discussed can be achieved independently in various embodiments of the present disclosure or may be combined in yet other embodiments further details of which can be seen with reference to the following description and drawings.

DETAILED DESCRIPTION

Figure 1:
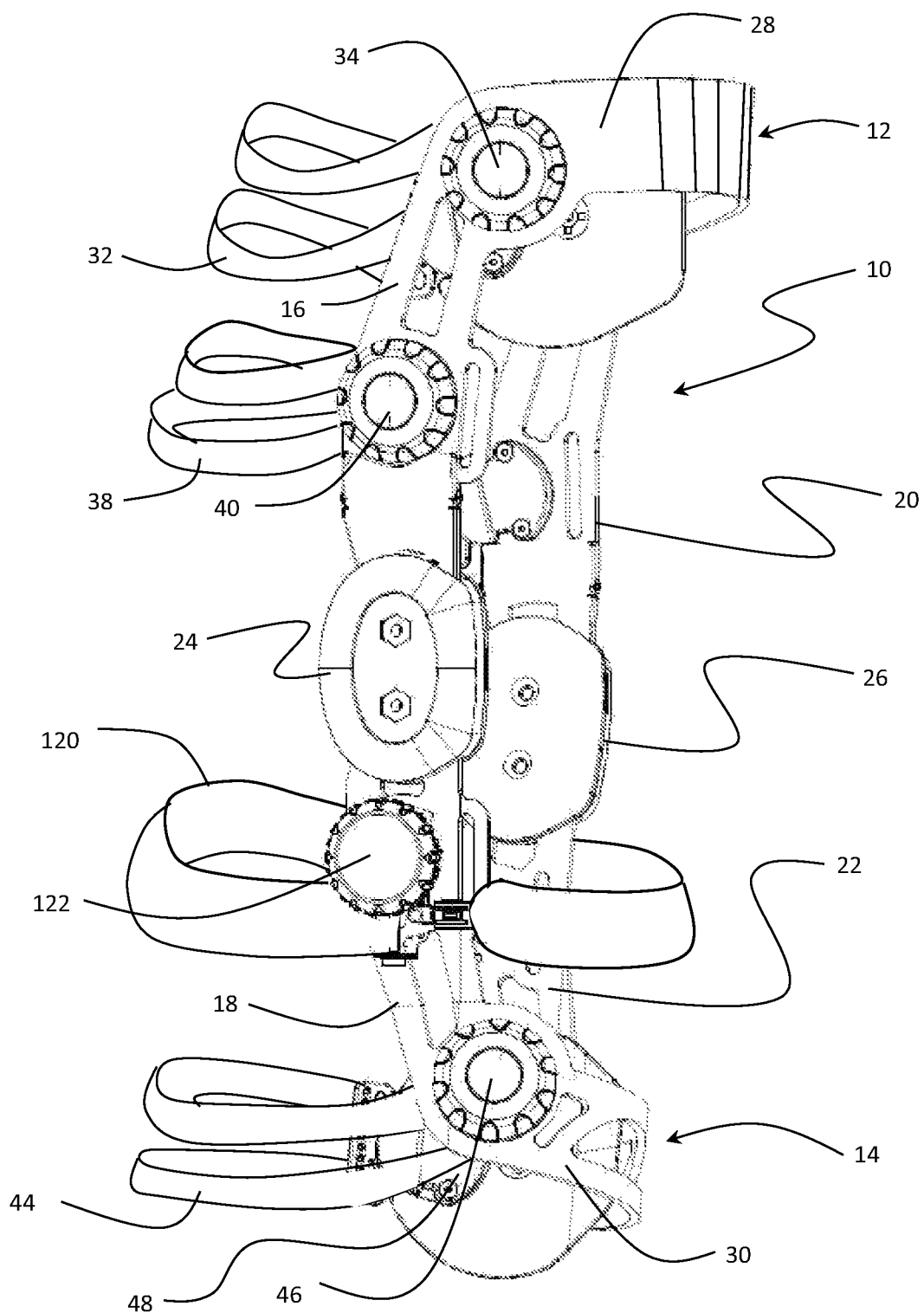
FIG. 1 is a lateral isometric views of an embodiment of an example orthopedic knee brace on which the present embodiments may be employed.

Embodiments disclosed herein provide a strap adjustment system for orthopedic braces which incorporates ratcheting tensioning elements and quick release attachments. Spring loaded retraction of straps is selectively accomplished for convenient storage to prevent entanglement warping of straps when not in use. Strap engagement features of the quick release attachments provide angular orientation relief for the straps when secured. As shown in FIG. 1, an example orthopedic knee brace 10 is composed of an upper attachment assembly 12 to be received on the thigh of the patient and a lower attachment assembly 14 to be received on the lower leg of the patient. Each attachment assembly (which is shown in detail in FIGS. 2A and 2B for the upper attachment assembly) incorporates a lateral support 16, 18 and a medial support 20, 22. Hinges 24 and 26 interconnect the lateral and medial supports, respectively, of the upper and lower attachment assemblies. Each attachment assembly includes an anterior arch support 28, 30.

Figure 2A:
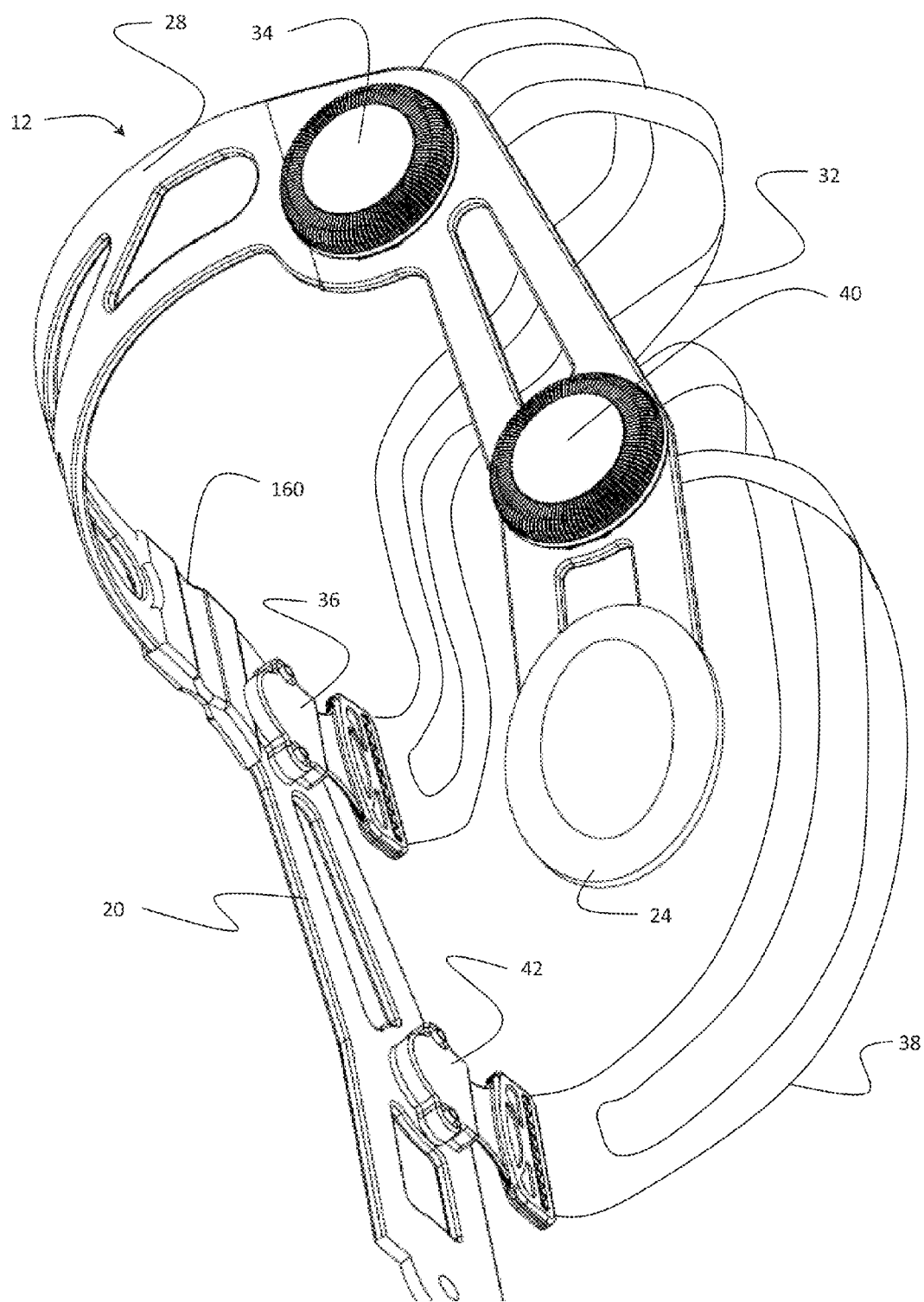
FIGS. 2A and 2B are lateral and medial isometric view of the upper attachment assembly.
Figure 2B:
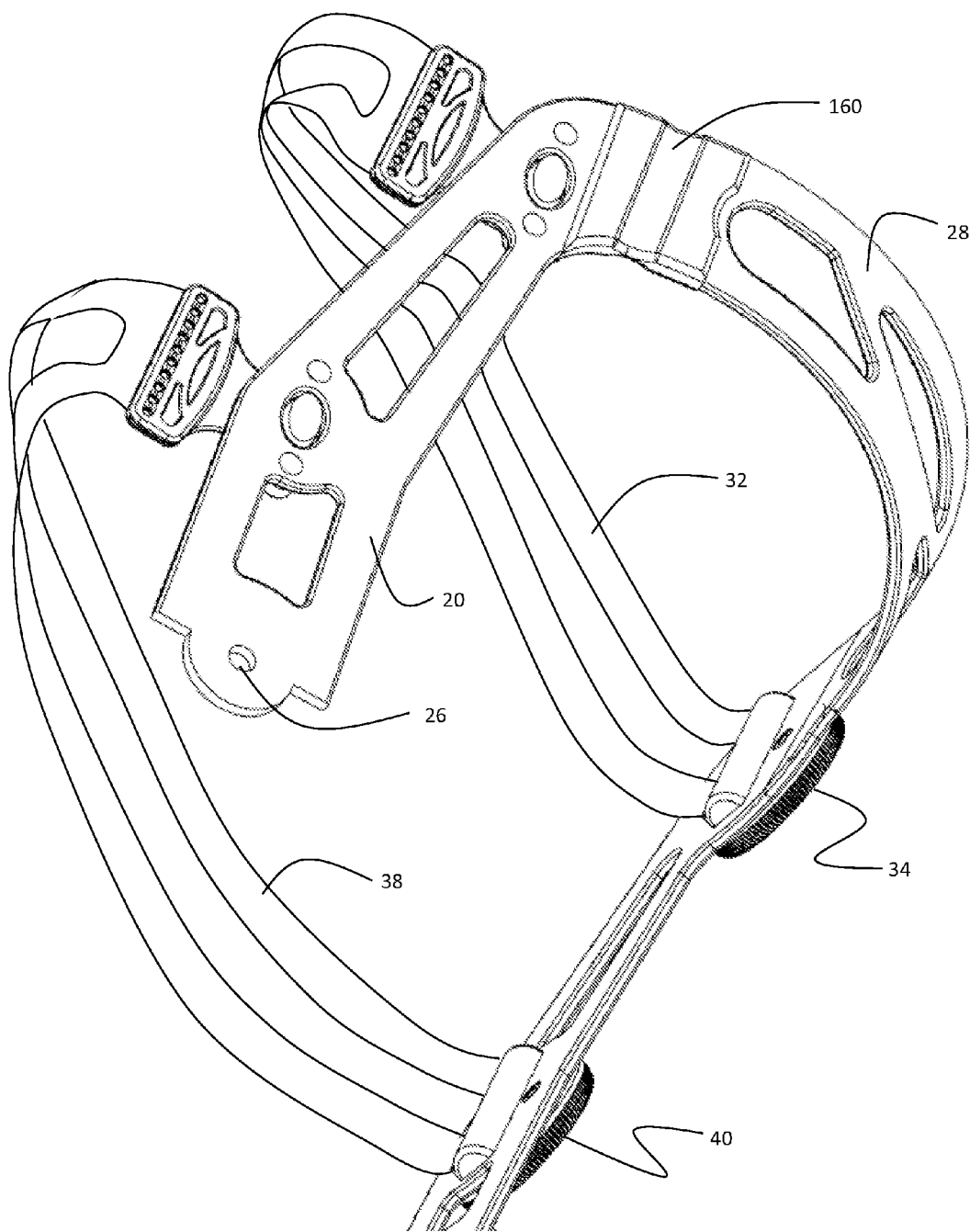

As shown in FIG. 1 (for a right leg brace) and additionally in FIGS. 2A and 2B (for a left leg brace to demonstrate use of the embodiment for either leg), the upper attachment assembly 12 for the example embodiment employs upper posterior strap 32 extending from an upper cinching system assembly 34 adjacent the anterior arch support 28 on the lateral side of the upper attachment assembly around the posterior of the thigh to a quick release attachment assembly 36 on the medial side of the upper attachment assembly adjacent the anterior support. Similarly, a lower posterior strap 38 extends from a lower cinching system assembly 40 adjacent the lateral hinge 24 on the lateral support element 16 around the posterior the thigh to a lower quick release attachment assembly 42 on the medial support element 20 adjacent the medial hinge 26.

As shown in FIG. 1 the lower attachment assembly 14 has a bottom posterior strap 44 extending from a bottom cinching system assembly 46 adjacent the anterior arch support 30 on the lateral side of the lower attachment assembly around the posterior of the calf to a quick release attachment assembly 48 on the medial side of the lower attachment assembly adjacent the anterior support.

Figure 3A:
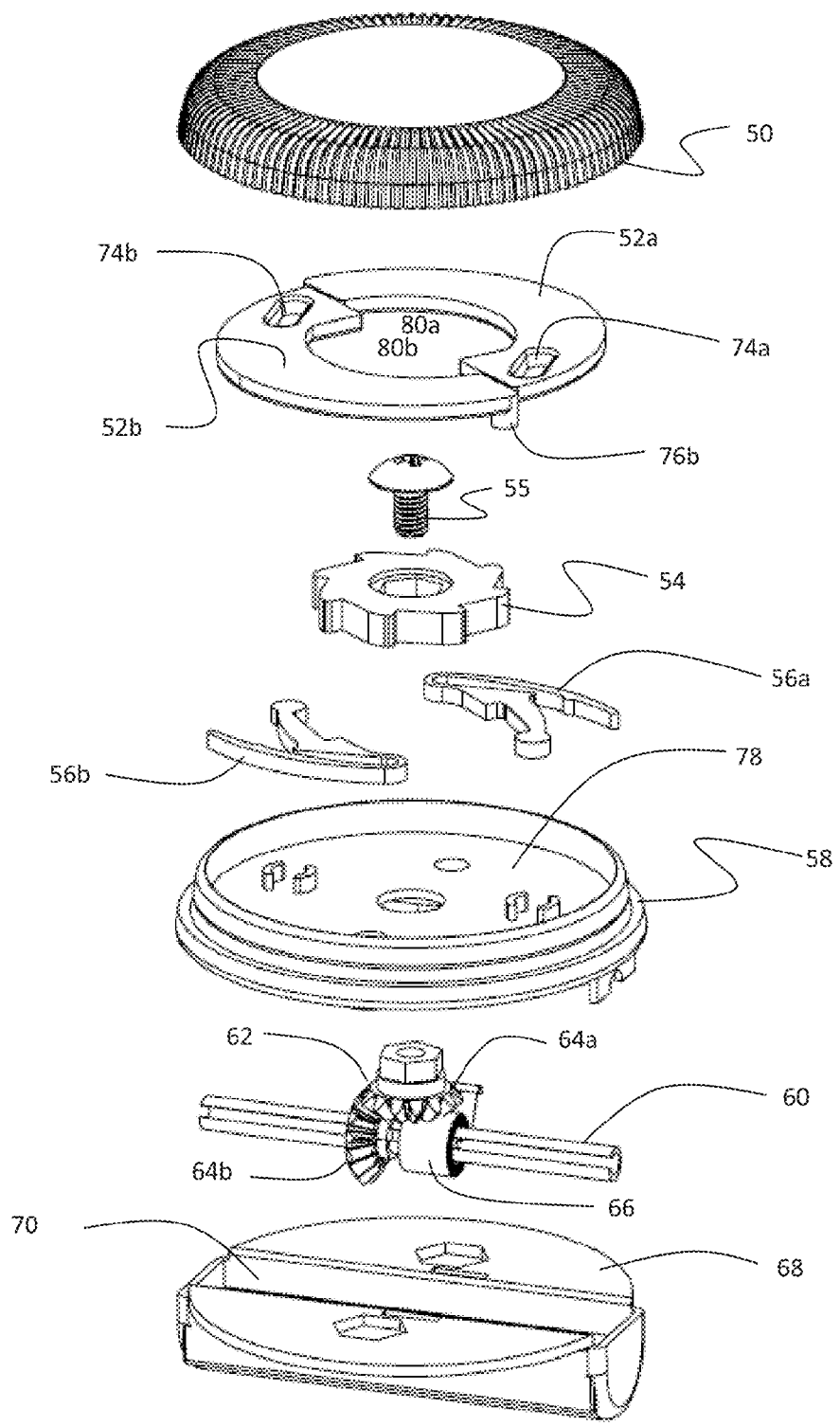
FIGS. 3A and 3B are downward exploded and upward exploded isometric views of a first embodiment of the cinching system assembly.
Figure 3B:
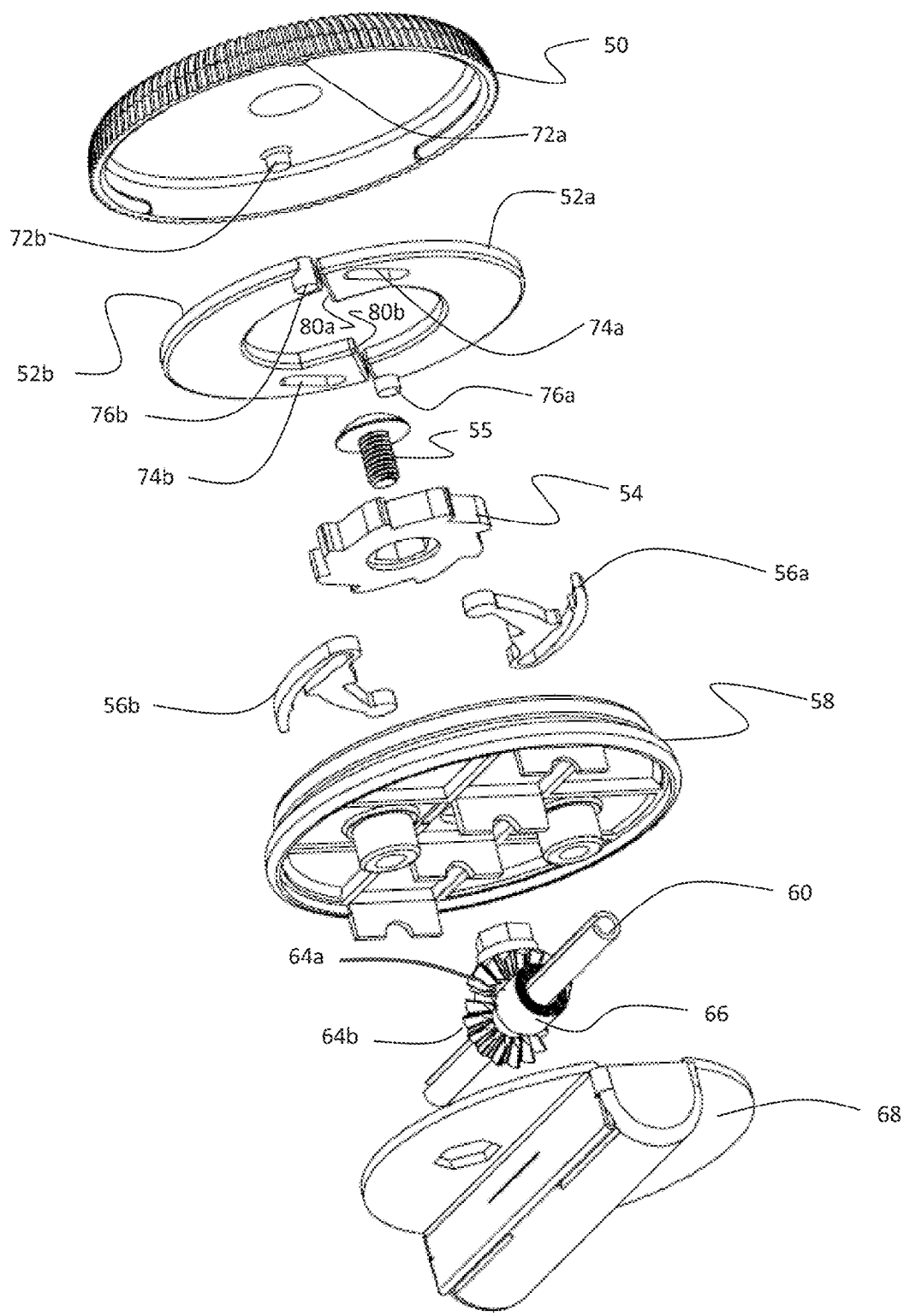
Figure 3C:
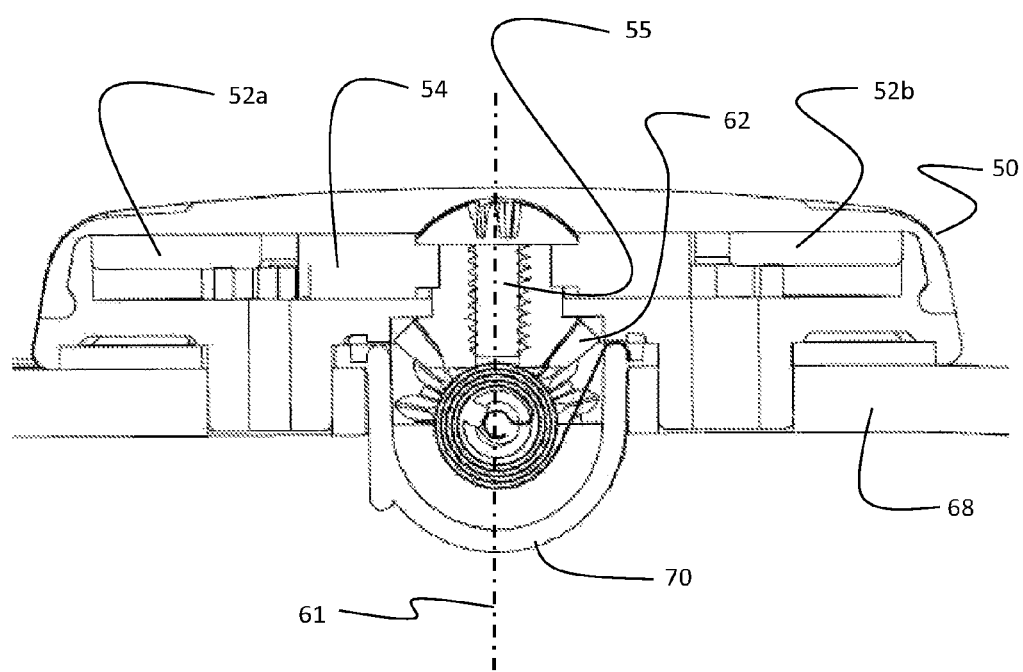
FIG. 3C is aside section view of the first embodiment.

The cinching system assemblies 34, 40 and 46 are identical for the example embodiment and are shown in detail in FIGS. 3A-8. As best seen in FIGS. 3A and 3B, each cinching system assembly incorporates a knob 50 which is rotated by the user to tension or retract the associated strap, as will be described in greater detail subsequently. Paired cinching plates 52a and 52b are operatively engaged and disengaged from a ratchet wheel 54. Paired ratchet arms 56a and 56b also releasably engage the ratchet wheel 54. The cinching plates, ratchet arms and ratchet wheel are constrained in a body top 58 over which the knob 50 is received. A slotted shaft 60 is employed for rolled storage and dispensing of the associated strap, as will be described in greater detail subsequently. A beveled gear set 62 is driven by the ratchet wheel 54 and attached to the shaft 60 having a first gear 64a engaged with the ratchet wheel 54 through the bolt 55 for rotation and a second gear 64b engaged to the shaft 60 for rotation of the shaft. A coil spring 66 is employed for rotational tensioning of the shaft 60 during dispensing to retract the strap upon release, as will be described in greater detail subsequently. Beveled gear set 62 allows an orthogonal orientation between the shaft 60 and an axis of rotation 61 of the knob 50 extending through the connecting bolt 55. A body bottom 68 provides a storage cavity 70 for the shaft 60 and associated strap.

Figure 4A:
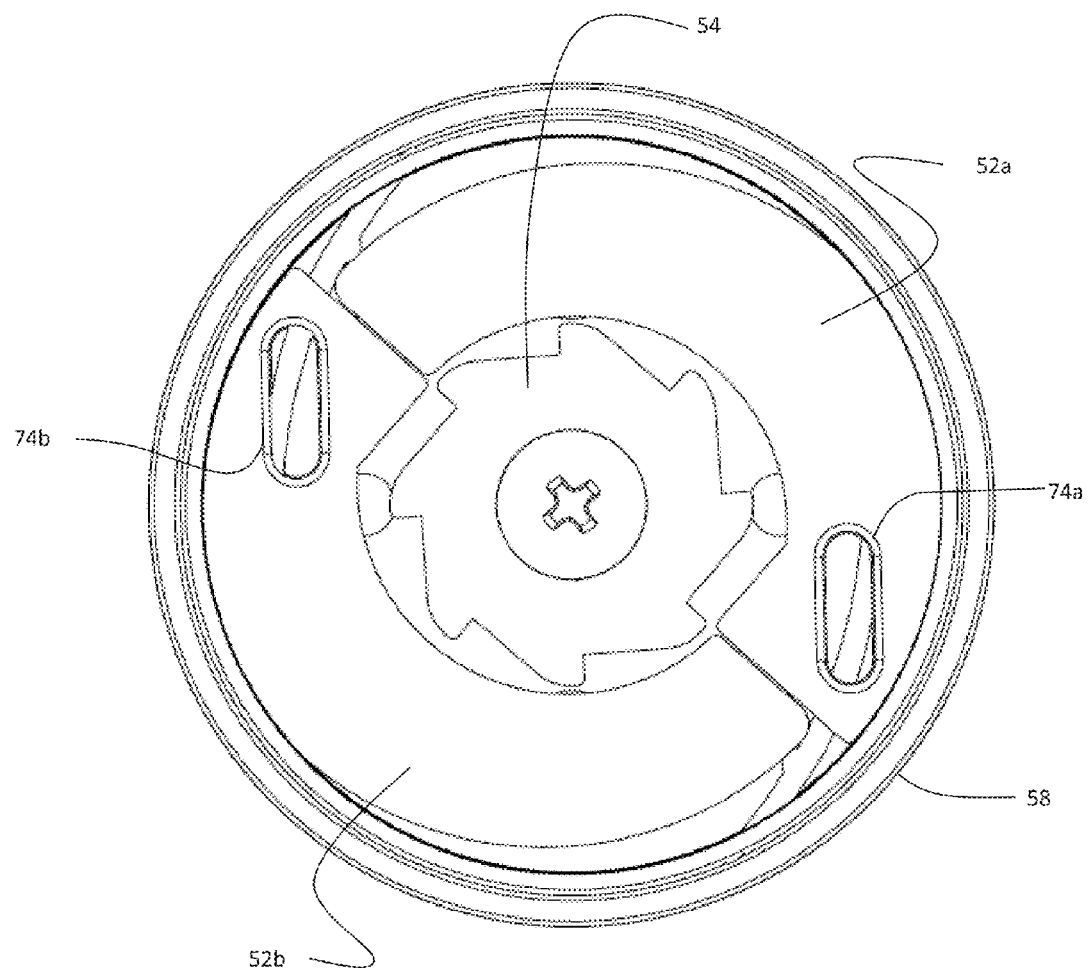
FIG. 4A is a top view of the cinching plates in the cinching system assembly in the disengaged position.
Figure 4B:
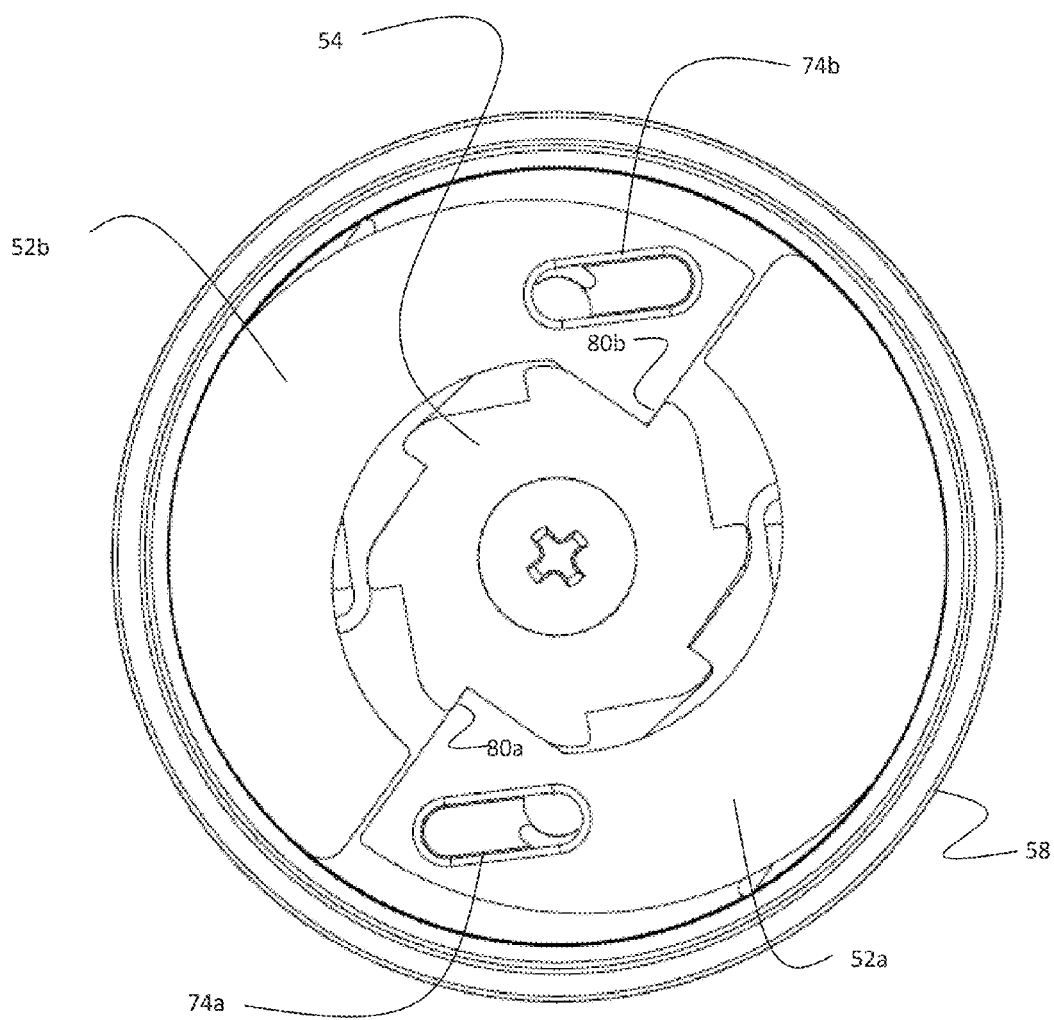
FIG. 4B is a top view of the cinching plates in the cinching system assembly in the engaged position.
Figure 5A:
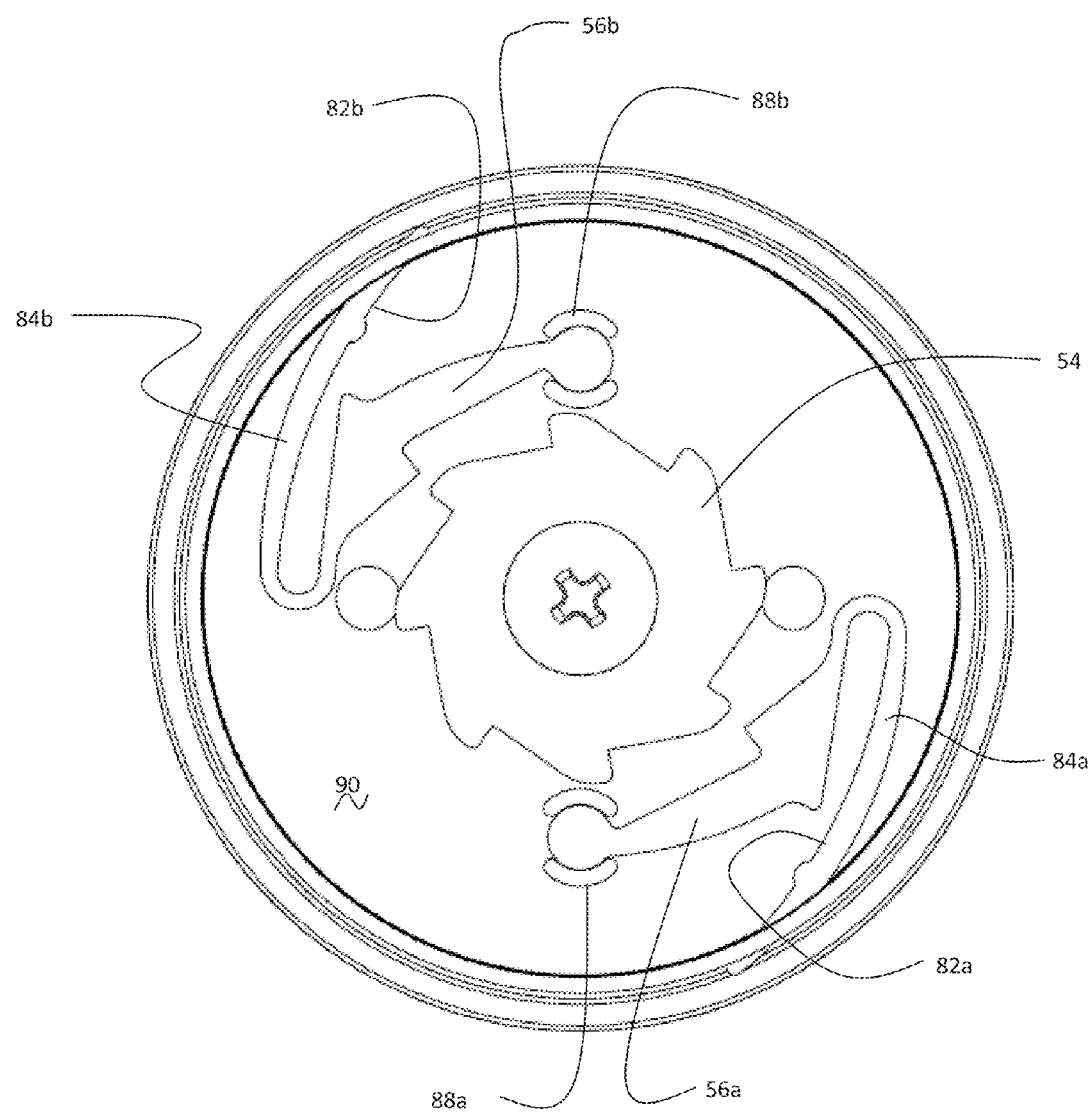
FIG. 5A is a top view of the ratchet arms in the cinching system assembly in the disengaged position.
Figure 5B:
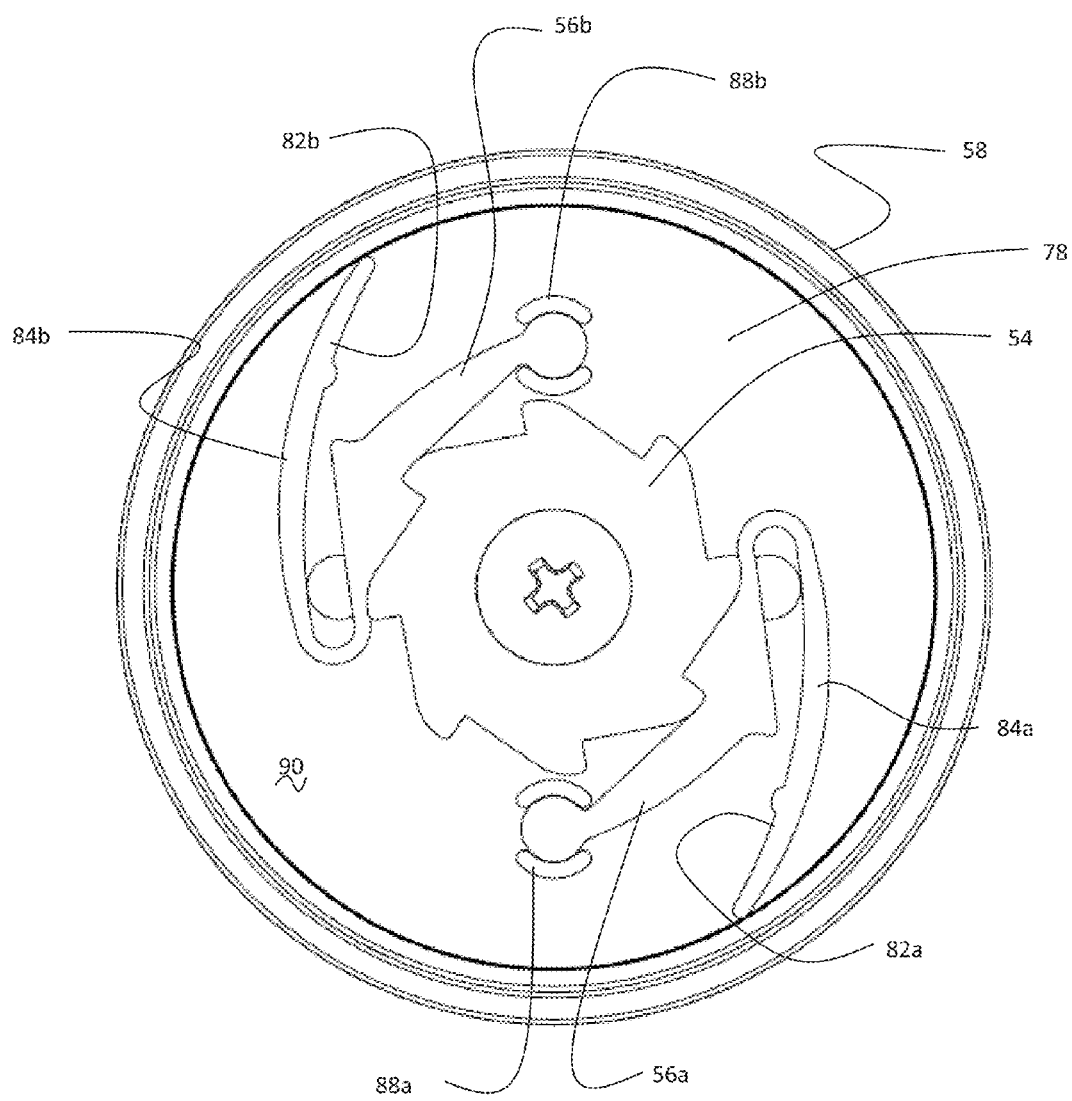
FIG. 5B is a top view of the ratchet arms in the cinching system assembly in the engaged position.

When the brace is first applied, the ratchet arms 56a, 56b and the cinching plates 52a, 52b have been moved away from the ratchet wheel 54 allowing the strap to be withdrawn from the shaft 60 of the associated cinching system assembly 34, 40, 46. The details of how the components achieve this position will be explained subsequently. The user will extend the strap from each cinching system assembly 34, 40 and 46 against the resistance of the coil spring 66 in each assembly. They will then insert the strap end into the associated quick release assembly 36, 42 or 48 (described in greater detail with respect to FIGS. 8-11 subsequently) on the opposite side of the brace. The spring 66 will then take up any slack in the strap. At this point the user will turn the knob 50 clockwise to tighten the strap to the desired tension. The knob 50 has two pins 72a, 72b (best seen in FIG. 3B) that extend down into slots 74a, 74b in the cinching plates 52a and 52b, respectively. The initial position of the cinching plates is shown in FIG. 4A. The cinching plates each have a pin 76a, 76b that extends down into the interior volume 78 of the body top 58 occupied by the ratchet arms 56a, 56b. At this point the cinching plate pins are holding the ratchet arms away from the ratchet wheel. When the knob is turned to the right the knob pins 72a, 72b slide along the slots 74a, 74b in the cinching plates 52a, 52b and cause the plates to move inward and engage the ratchet wheel 54 with contact faces 80a, 80b as shown in FIG. 4B. As the knob 50 continues to be turned clockwise the ratchet wheel 54 turns the gear set 62 causing the straps to be tightened around the slotted shaft 60. Meanwhile the pins 76a, 76b that extend down from the cinching plates 52a and 52b, respectively, slide off contact surfaces 82a and 82 on the spring arms 84a, 84b allowing the ratchet arms 56a, 56b to also engage the ratchet wheel 54. For the embodiment shown, spring arms 84a and 84b are integral with ratchet arms 56a, 56b which include pivot pins 86a, 86b received in retainers 88a and 88b extending from the surface 90 of body top 58. As the knob 50 continues to be turned the cinching plates 52a, 52b rotate urged by pins 76a and 76b in the slots 74a, 74b and cause the ratchet wheel 54 to turn which in turn causes the gear set 62 and slotted shaft 60 to turn and tighten the strap. Rotation in this direction will cause the cinching plate pins to slide past the spring arms 84a, 84b causing them to flex as passed, snapping back into a more relaxed position when passed. The spring arms 84a, 84b urge the ratchet arms 56a, 56b to maintain contact with the ratchet wheel 54. When the knob 50 is released the ratchet arms 56a, 56b prevent the ratchet wheel 54, gears 62 and slotted shaft 60 from rotating in the opposite direction therefor maintaining tension on the straps.

When it is time to remove the brace, the quick release buttons are pushed, as will be described in greater detail subsequently, releasing the straps and allowing the brace to be removed. To retract the straps and ready the brace and system to be re-applied, the knob 50 is turned to the counterclockwise about a half turn until it stops. This rotation caused the knob pins 72a, 72b to slide in slots 74a, 74b in the cinching plates 52a, 52b the opposite direction which causes the plates to move away from the ratchet wheel. Once the pins 72a, 72b hit the end of the slots 74a, 74b the plates will start to rotate. Within a half revolution the cinching plate pins 76a, 76b will encounter the contact surfaces 82a, 82b of the spring arms 84a, 84b of each ratchet arm 56a, 56b. As the knob 50 is continues to be turned counterclockwise the pins 76a, 76b will ride up the contact surfaces 82a, 82b of the spring arms 84a, 84b pulling the ratchet arms 56a, 56b away from the ratchet wheel allowing the coil spring 66 which was tightened during withdrawal of the strap to wind in the strap. The brace is now in the same state as initially described.

Figure 6:
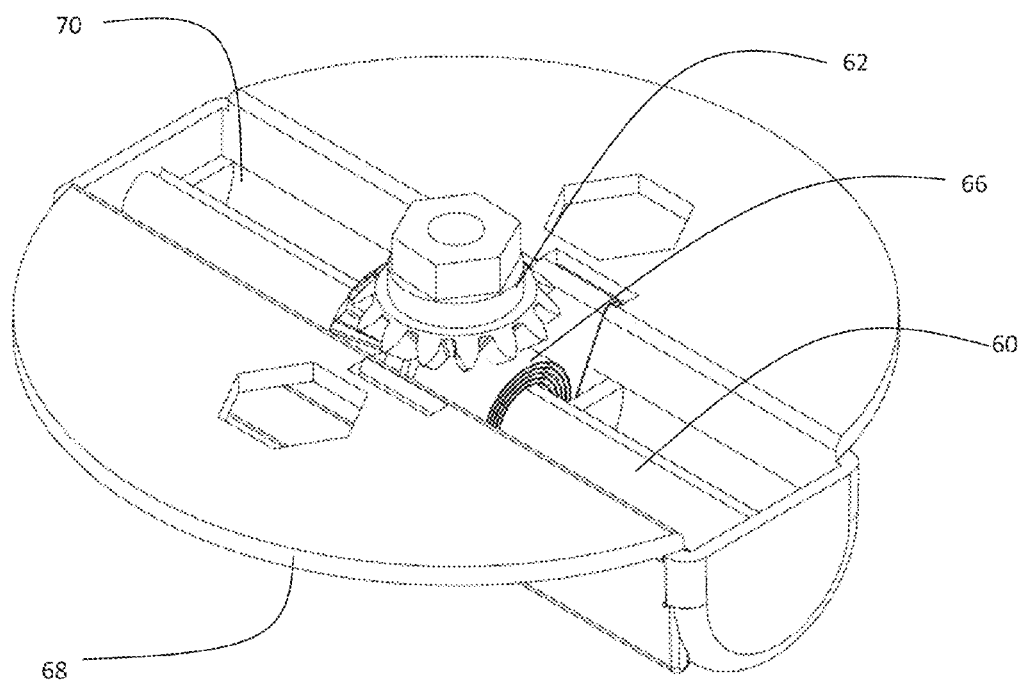
FIG. 6 is a top isometric detail of the body bottom of the cinching system assembly with the gear assembly, shaft and coil spring.
Figure 7:
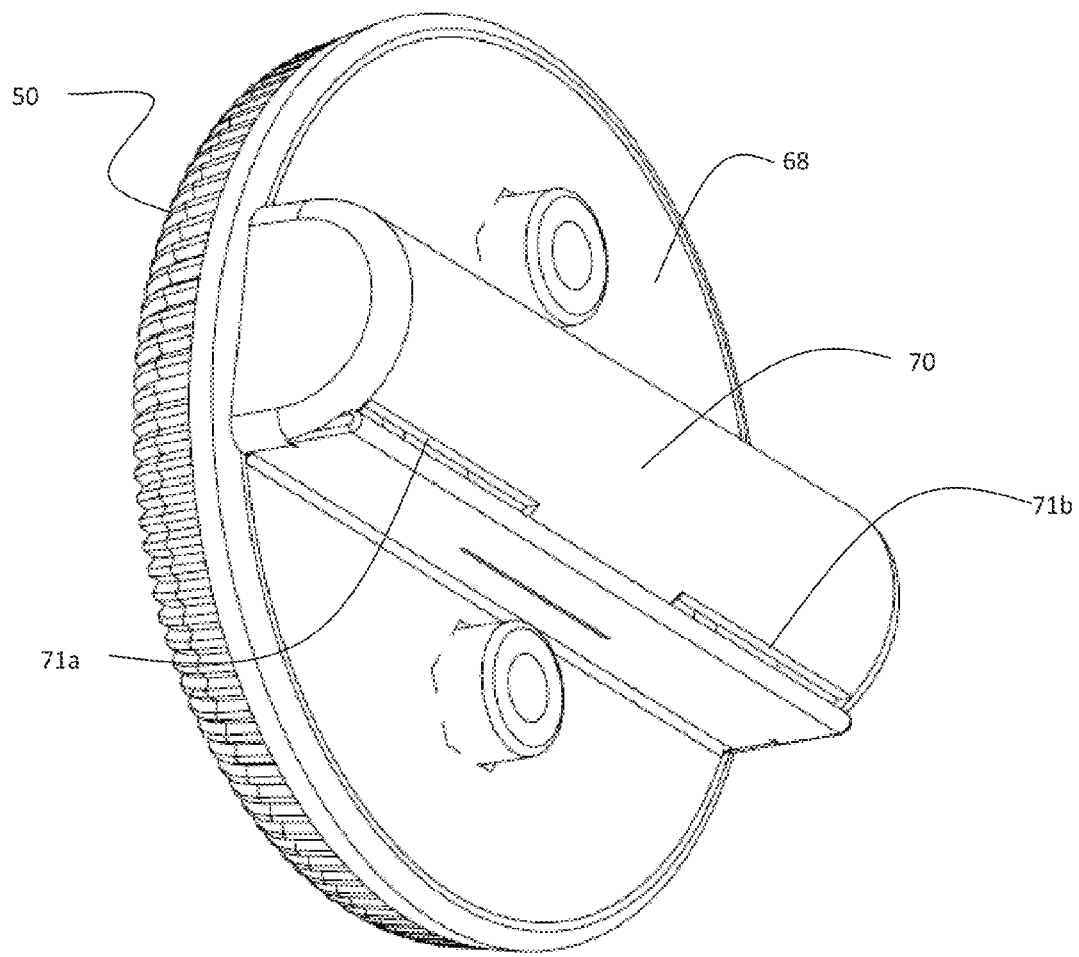
FIG. 7 is a bottom isometric detail of the cinching system assembly.

FIGS. 6 and 7 provide additional detail on the body bottom 68 which houses the slotted shaft 60 in the storage cavity 70. The storage cavity provides sufficient volume for the strap in the retracted condition when wrapped around the slotted shaft 60. To provide clearance and operation of the centrally located gears 62 and coil spring 66, the strap incorporates two parallel bands as shown in FIGS. 1A, 1B, 2A and 2B which are engaged on opposite ends of the slotted shaft. As seen in FIG. 7, two exit slots 71a and 71b are provided for the strap bands.

While described as a clockwise tightening system for typical right handed operation, the elements of the cinching system assemblies 34, 40 and 46 may be fabricated in mirror image to operate in a counterclockwise tightening system for left handed operation.

Figure 8:
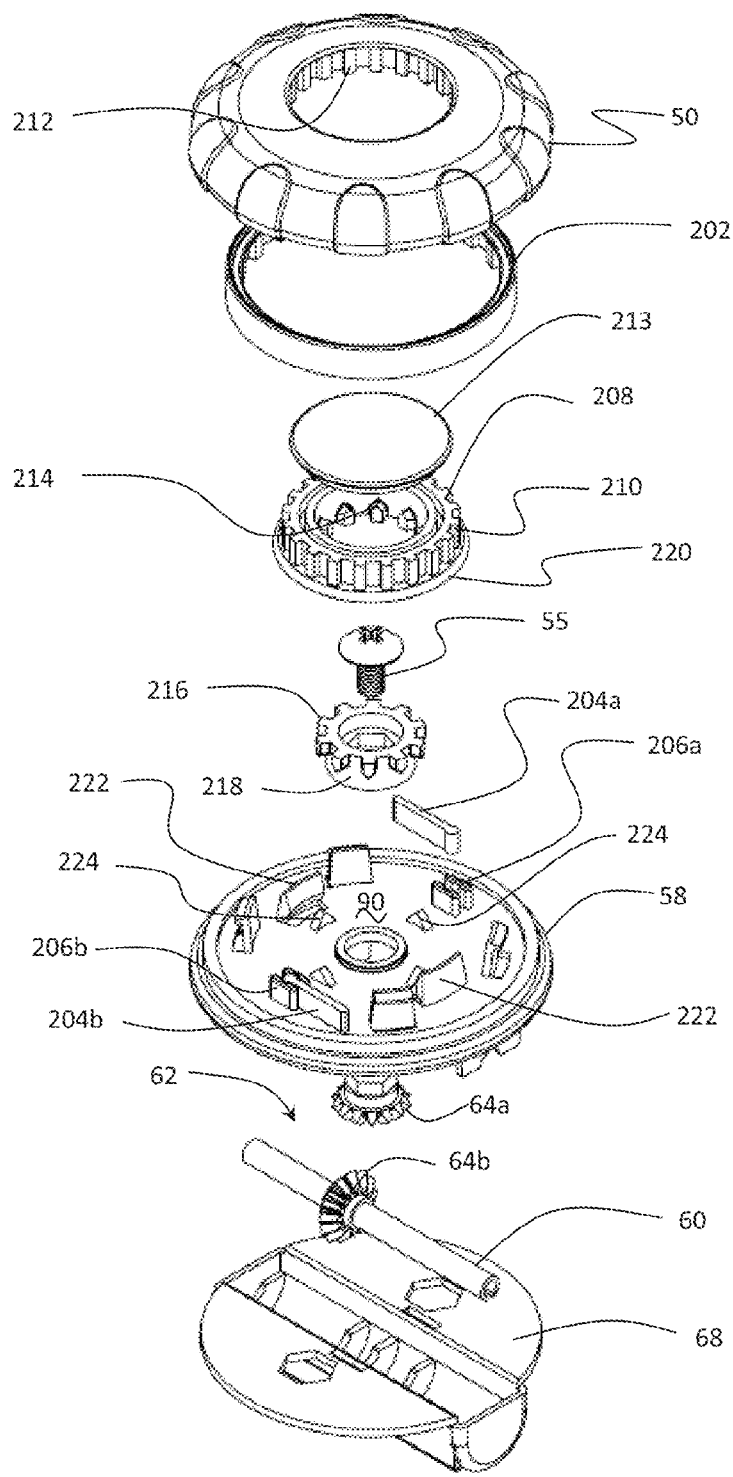
FIG. 8 is an exploded isometric view of a second embodiment of the cinching system assembly.
Figure 9A:
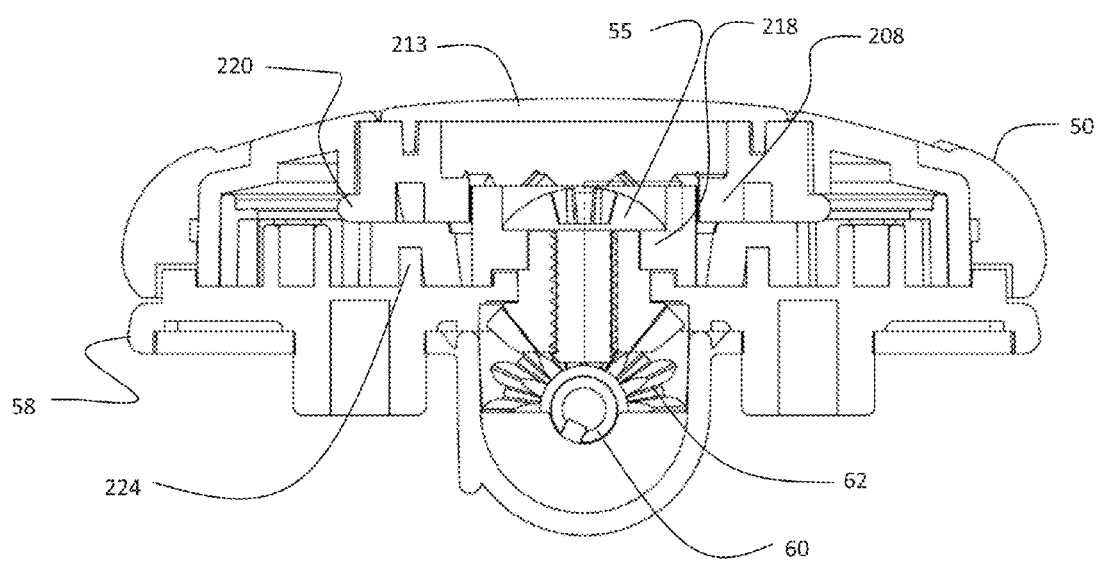
FIG. 9A is a side section view of the embodiment of FIG. 8 with the rotation teeth engaged.
Figure 9B:
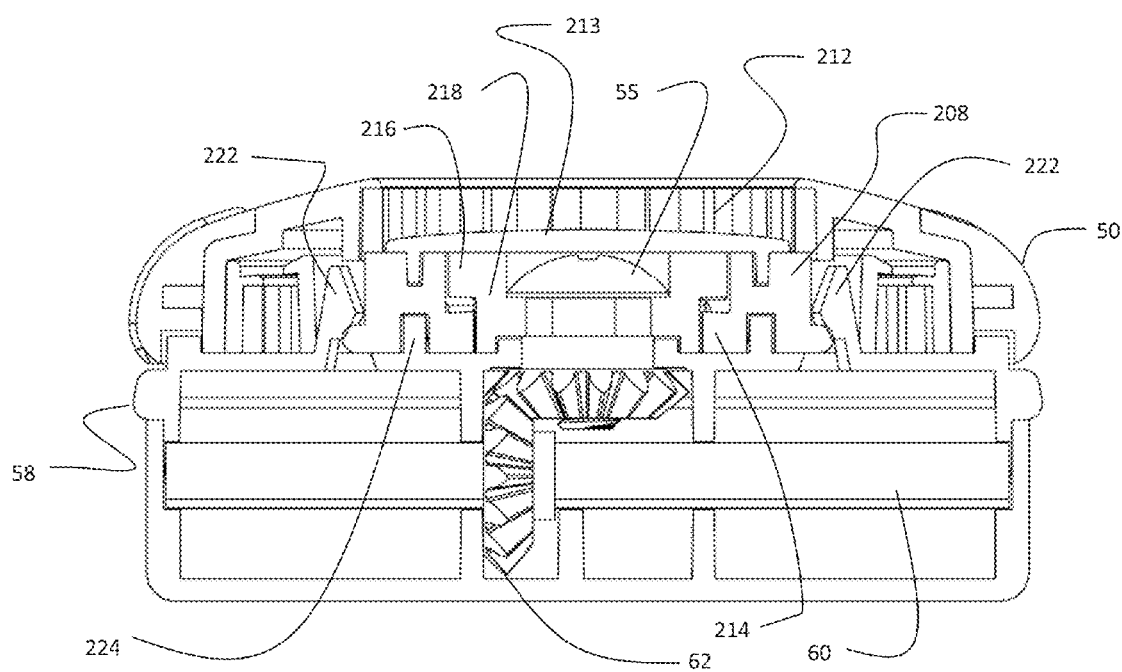
FIG. 9B is aside section view of the embodiment of FIG. 8 with the rotation teeth disengaged.

A second embodiment for the cinching system assembly with a push button release is shown in FIGS. 8 and 9A, 9B. As with the first described embodiment, the shaft 60 is rotated by a gear set 62 with bevel gears 64a and 64b driven by a bolt 55. However, the engagement element for transferring rotation of the knob 50 to the gear set 62 is an assembly including a ratchet ring 202 engaged within the knob 50 which is constrained by pawls 204a and 204b mounted in retainers 206a and 206b. The directional orientation of the pawls allows rotation of the knob 50 and associated ratchet ring 202 in only one direction. An engagement ring 208 having an external spline 210 is received by an internal spline 212 in the knob 50. Engagement ring 202 is vertically depressable from a first position as shown in FIG. 9A to a second position shown in FIG. 9B using a button 213. In the first position internal teeth 214 on the engagement ring 208 engage a tooth set 216 on gear drive ring 218 connected to the gear set 62 by bolt 55. In the first position, rotation of knob 50 therefore imparts rotation of the gear set 62 rotating shaft 60 to tighten the strap element (32, 38 of FIGS. 2A, 2B) on the shaft. Pawls 204a and 204b engaging ratchet ring 202 prevent loosening of the strap element. Depressing engagement ring 202 to the second position as shown in FIG. 9B disengages internal teeth 214 on the engagement ring 208 from tooth set 216 on the drive ring 218 allowing drive ring to freely rotate. In the second position with engagement ring 208 depressed, the strap element may be extracted from shaft 60.

As shown in FIGS. 9A and 9B, a snap shelf 220 encircling a lower periphery of engagement ring 208 is engaged in the second position by resilient retainers 222 extending from surface 90 of body top 58 to maintain the engagement ring in the depressed second position. Rotation of the knob 50 rotates engagement ring 208 for operable contact with ramps 224 extending from surface 90 urging the engagement ring upwards disconnecting snap shelf 220 front the resilient retainers 222 and returning engagement ring 208 to the first position, for operable reengagement of tooth set 216 on drive ring 218 with the internal teeth 214 on engagement ring 208.

Figure 10:
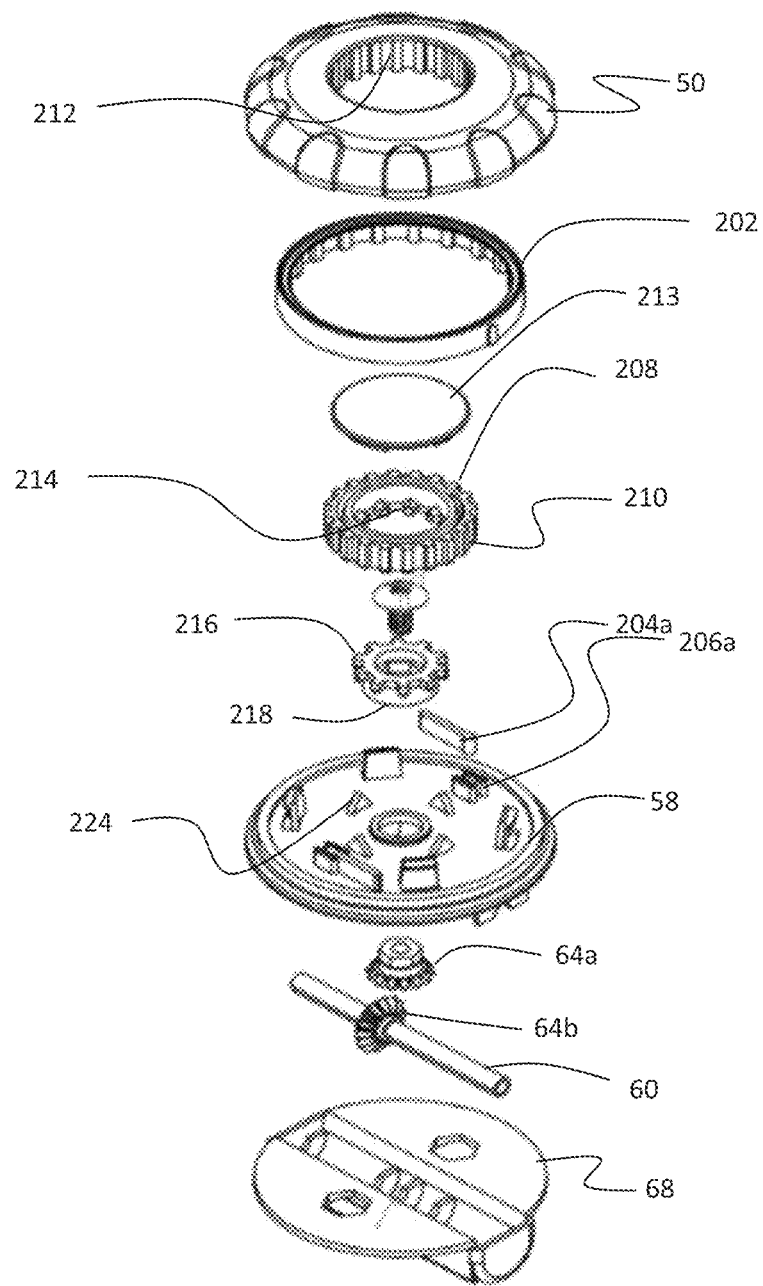
FIG. 10 is an exploded, isometric view of a third embodiment of the cinching system assembly.
Figure 11:
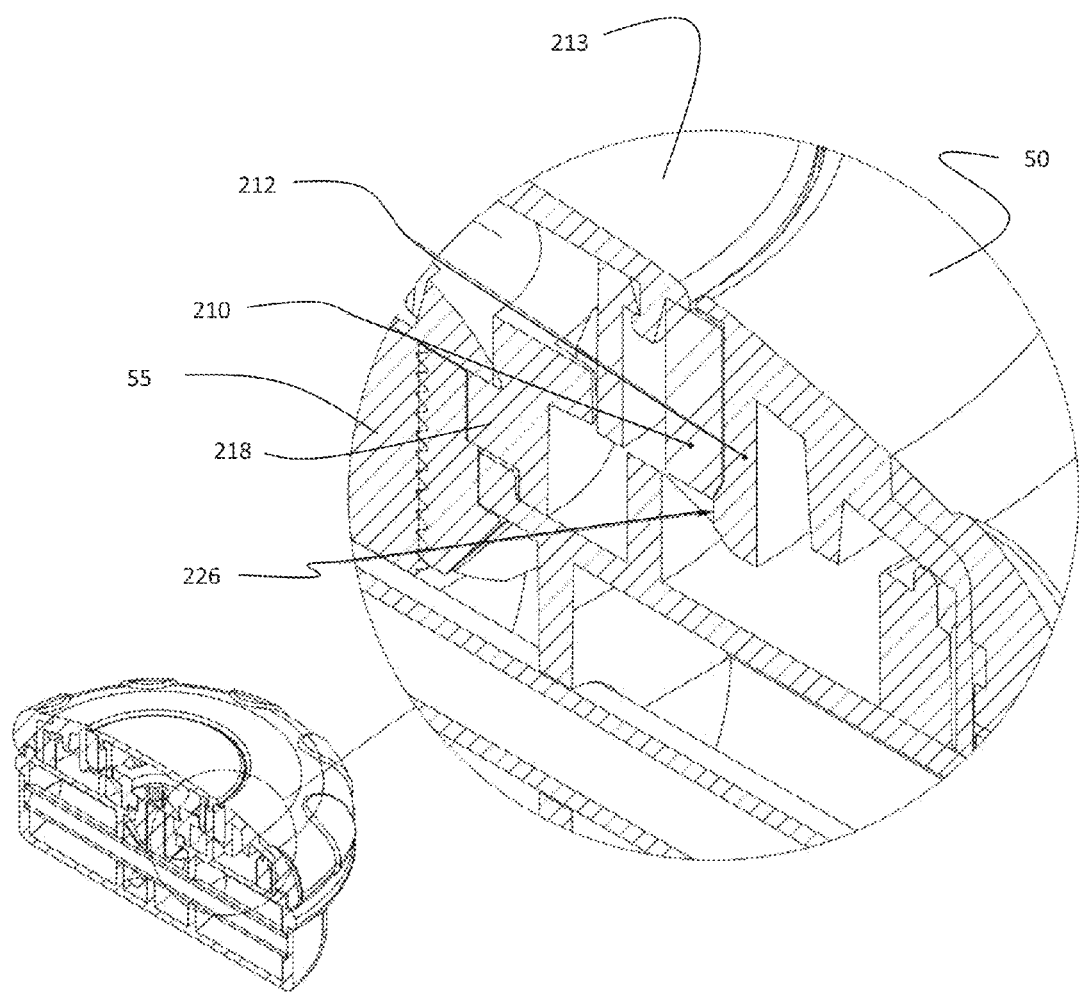
FIG. 11 is a side section view of the embodiment of FIG. 10 with the rotation teeth engaged.

A third embodiment for the cinching system employing the push button release with an alternative engagement element retainer is shown in FIGS. 10 and 11. Elements and operation of the third embodiment are substantially identical to the second embodiment described above however, snap shelf 220 has been eliminated and one or more snap features 226, seen in FIG. 11 extending across selected teeth of spline 212 support associated teeth on the external spline 210 of engagement ring 208. Depressing engagement ring 208 with button 213 resiliently displaces snap feature 226 for passage of the associated tooth of spline 210 into the depressed second position. Frictional engagement of the snap features 226 on the external spline 210 retains the engagement ring in the depressed second position until rotation of the knob 50 engages ramps 224 to urge the engagement ring 208 back to the first position as previously described.

In each of the cinching system embodiments, rotation of the knob 50 in the tightening direction automatically reengages the ratcheting elements of the cinching system for tightening the strap.

Figure 12:
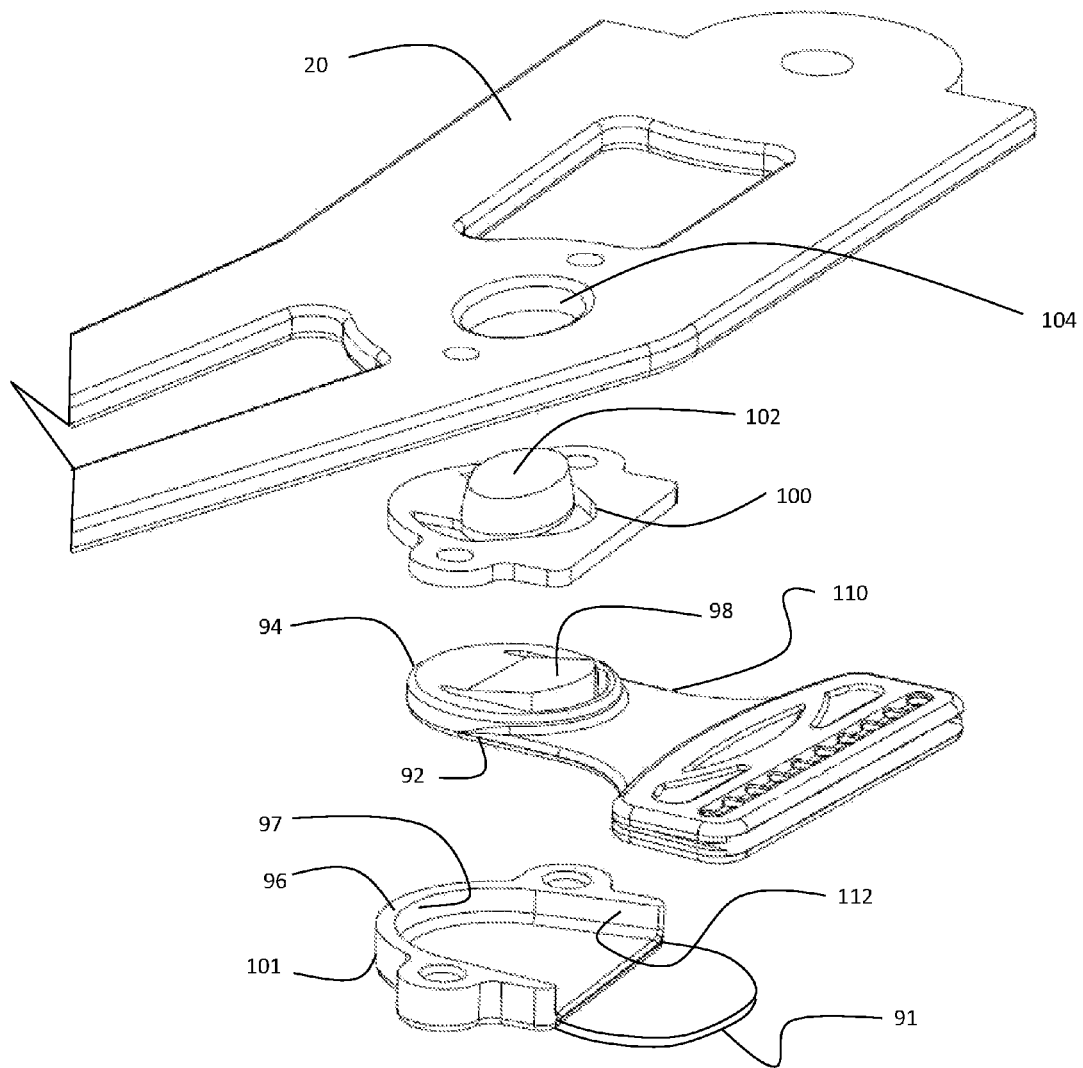
FIG. 12 is an exploded isometric of the quick disconnect assembly.
Figure 13:
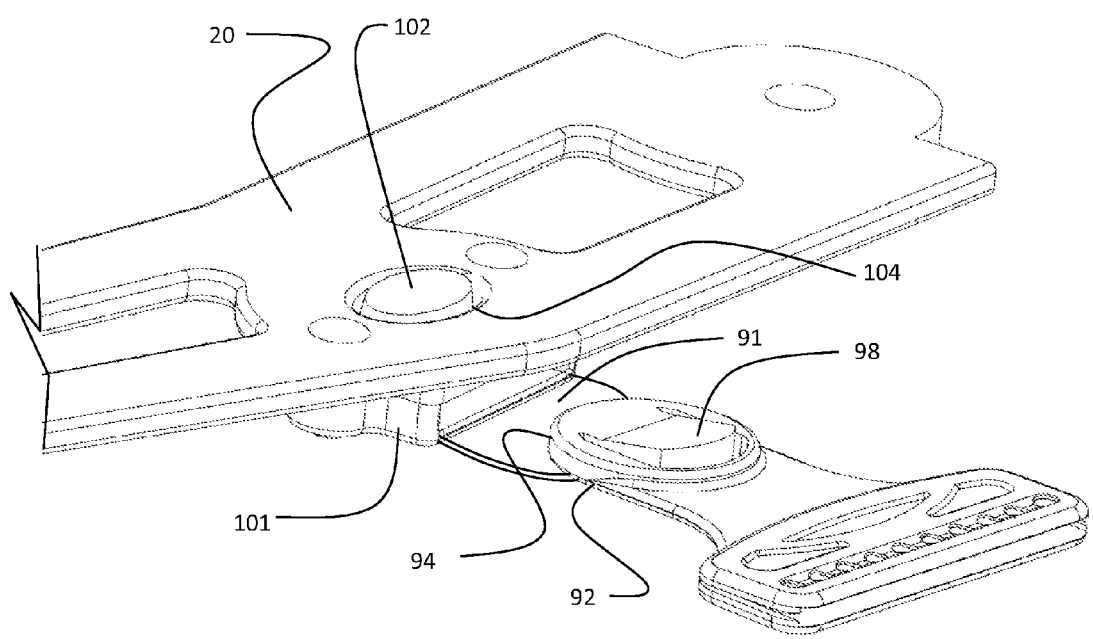
FIG. 13 is an isometric of the quick disconnect assembly with the strap tip disconnected.
Figure 14:
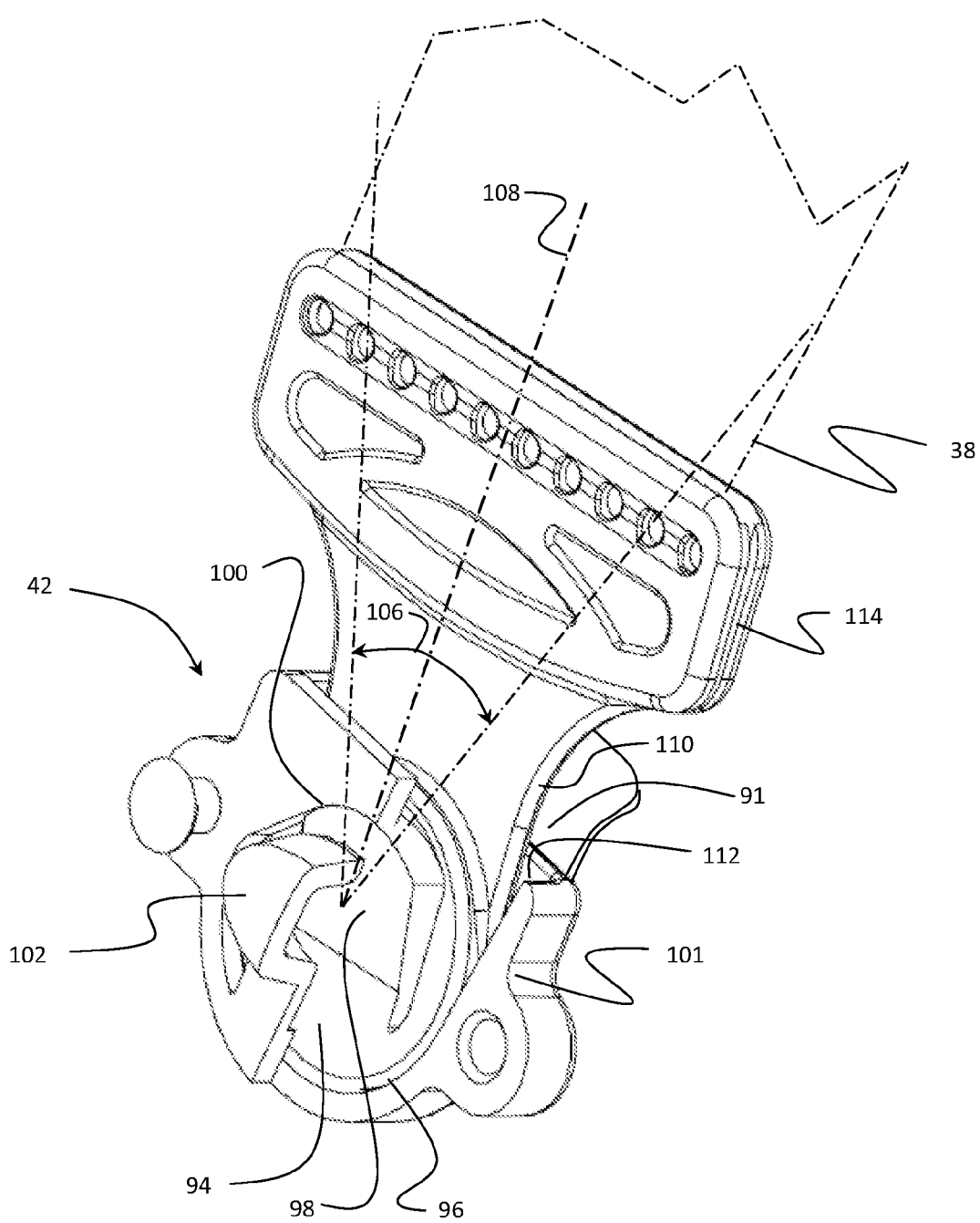
FIG. 14 is an isometric partial section view showing detail of the release button and resiliently depressible tongue on the strap tip.

The quick disconnect assemblies 36, 42 and 48 described with respect to FIGS. 1A and 1B are shown in detail in FIGS. 12-15. As shown in FIG. 12, quick disconnect assembly (assembly 42 shown as an example) is mounted to the medial longitudinal supports (upper attachment assembly 12 medial longitudinal support 20 shown as an example). A capture shoe 101 with a guidance flap 91 is attached to the medial support 20 to receive a strap tip 92. The inserted end 94 of the tip 92 is substantially semi-circular and the receiving end 96 of the shoe also has a semi-circular profile. For the embodiment shown, receiving end 96 incorporates a resilient leaf spring 97 engaging inserted end 94 to assist in ejection of the tip 92 upon release as described subsequently A resiliently depressible tongue 98 extends from a surface of the tip to be engaged in a capture bracket 100. A release button 102 resiliently mounted to the capture bracket may be depressed to resiliently deform and flatten the tongue 98 into the tip releasing it from the capture bracket. Leaf spring 97, resiliently engaged by the tip 92 upon insertion, urges the tip 92 out of the capture shoe 101 upon flattening of the tongue 98. For the embodiment shown, the button 102 extends through a mating hole 104 in the medial support 20 as shown in FIG. 13 allowing the quick release to be mounted on the interior surface of the medial support. FIG. 14 shows a partial cutaway view of the quick disconnect assembly showing engagement of the button and tongue to release the tongue from the capture bracket 100.

The semi-circular profiles of the inserted end 94 of the tip 92 and the receiving end 96 of the capture shoe 101 provide the ability for the tip 92 to swivel in the capture shoe through an angle 106 about a nominal insertion axis 108 before contact between a neck 110 extending from the tip 92 and walls 112 of the insertion slot in the capture shoe thereby allowing the associated strap (38 for the example shown in FIG. 14) to assume a natural angle about the posterior portion of the leg without bending or cutting into soft flesh.

Figure 15:
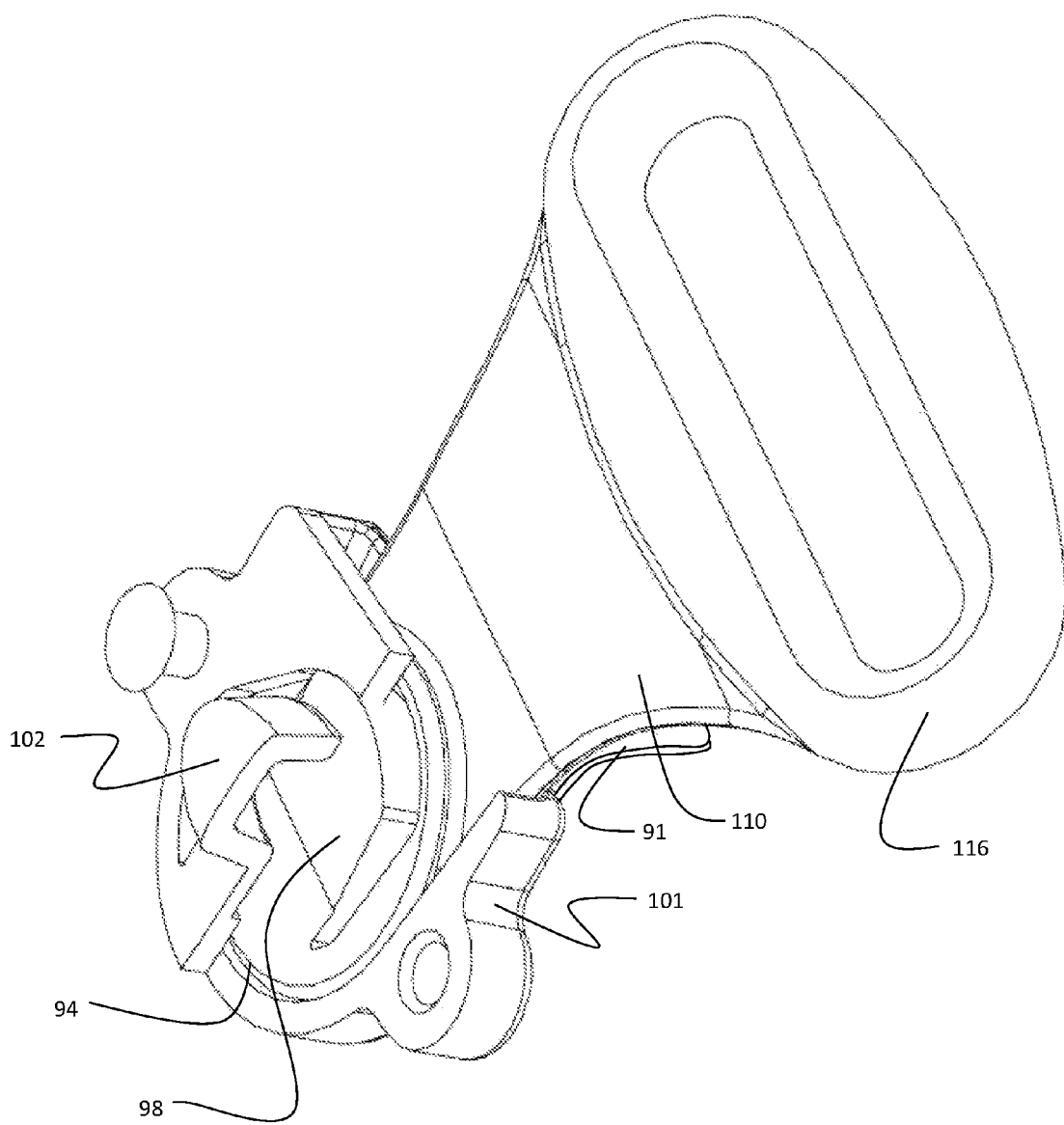
FIG. 15 is an isometric view of a second embodiment of the strap tip employing a D-ring extending from the neck.

The neck 110 terminates in a flanged attachment 114, as shown in FIG. 14, into which the strap 38 is secured by sewing or similar means. Alternatively, the neck 110 may terminate in a D-ring 116 as shown in FIG. 15 through which a strap may be inserted, folded back and connected to itself with hook and loop fasteners or similar means.

Figure 16:
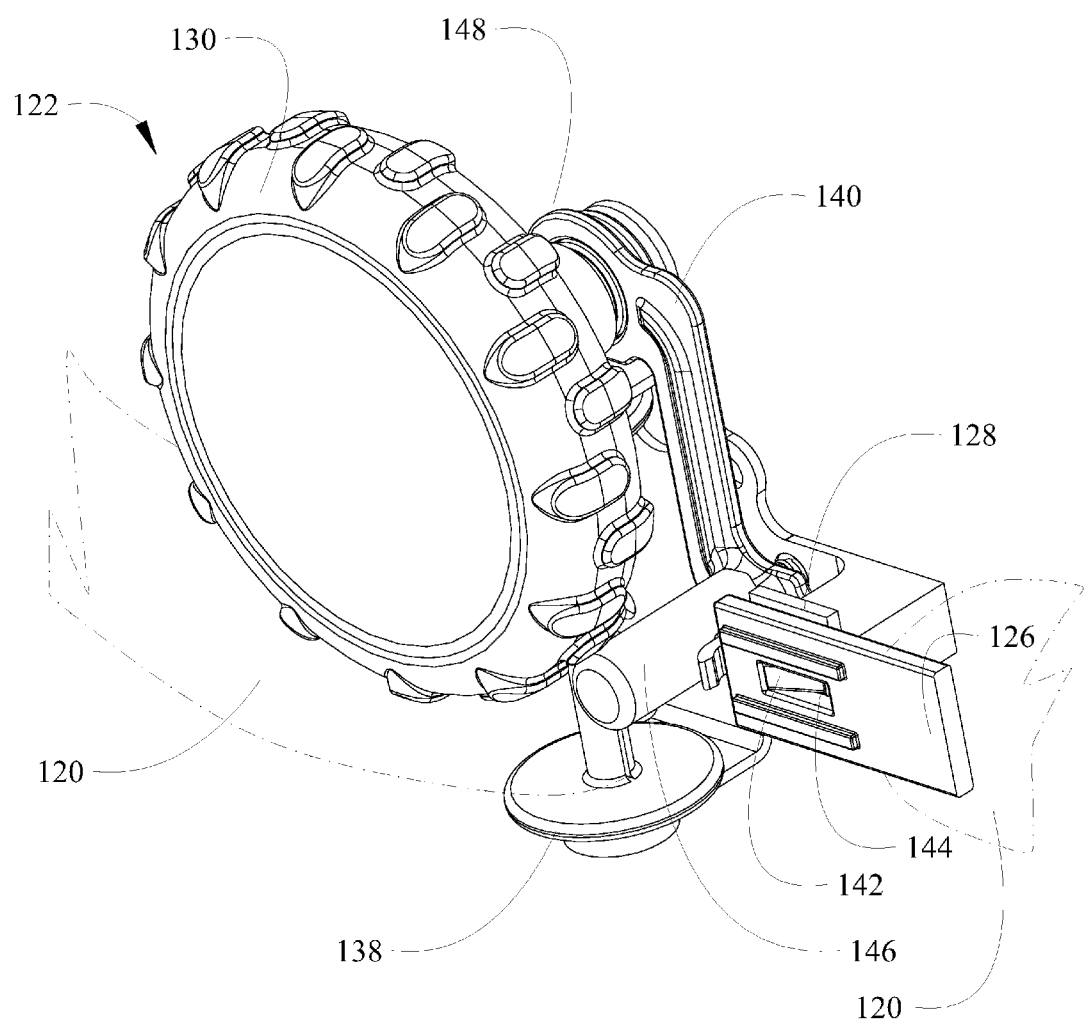
FIG. 16 is an isometric view of the single point tensioning system.
Figure 17:
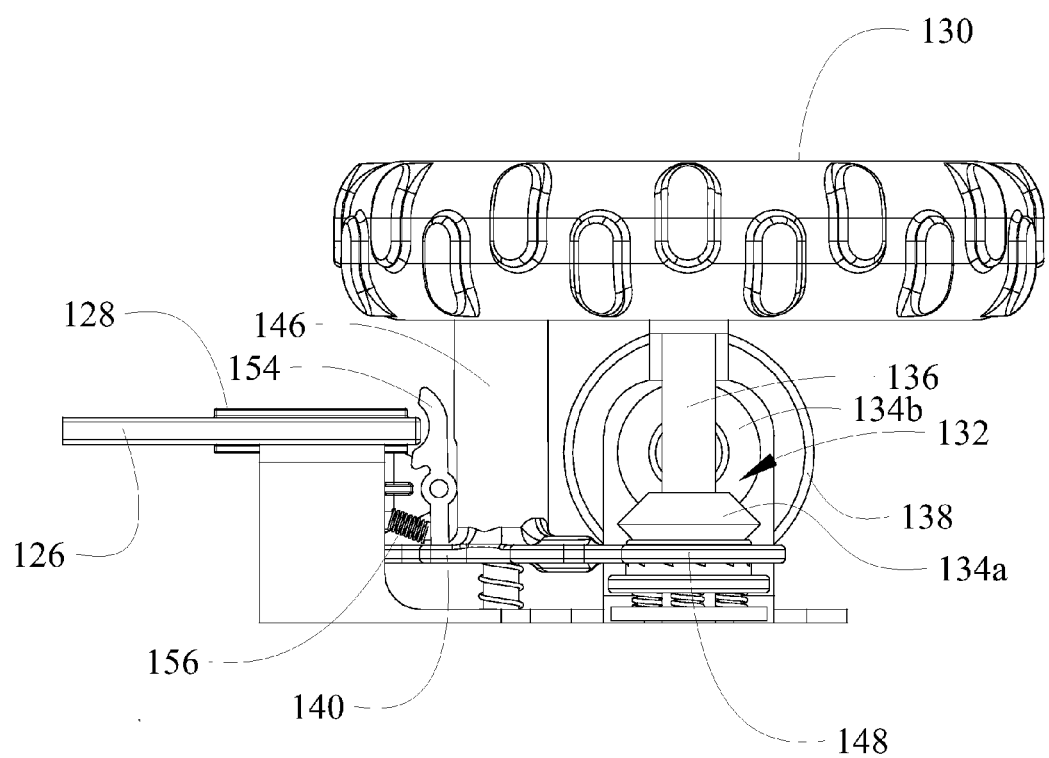
FIG. 17 is a top view of the single point tensioning system.
Figure 18:
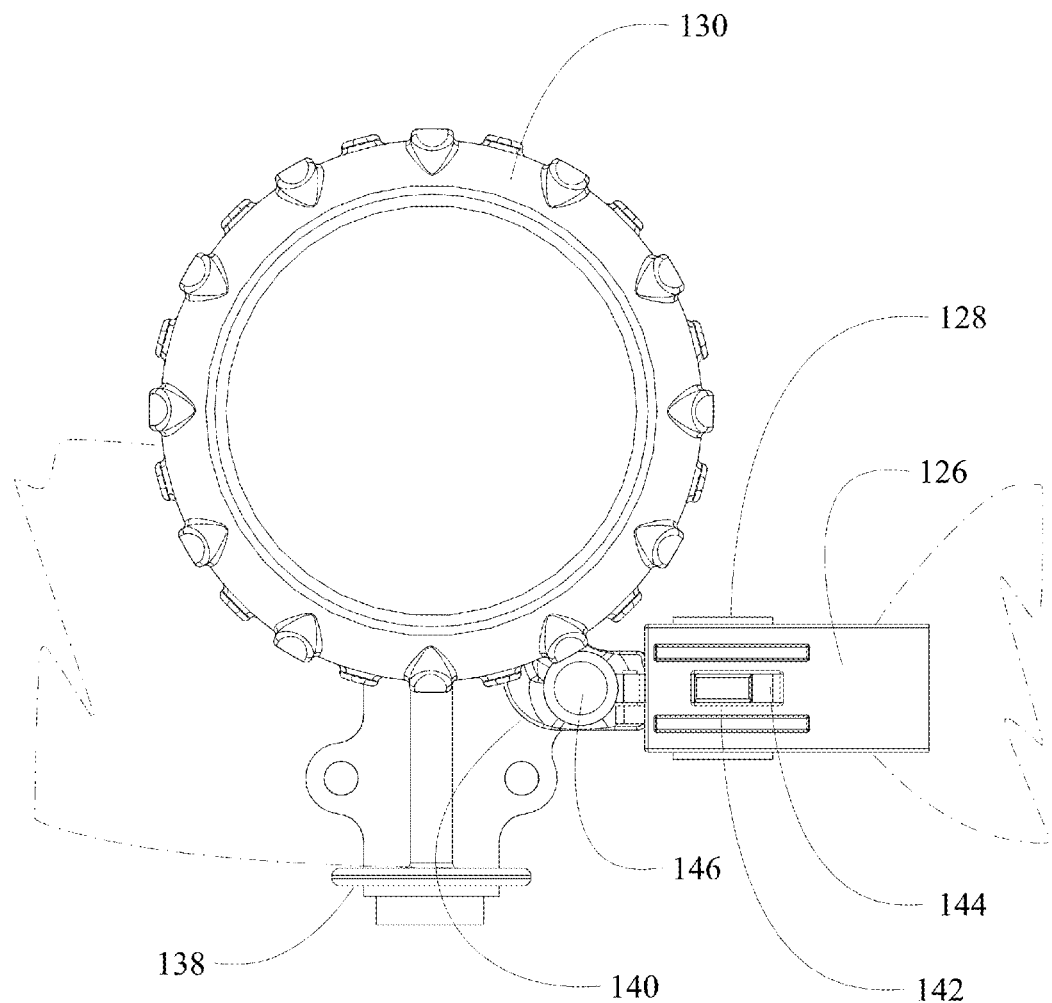
FIG. 18 is a side view of the single point tensioning system.
Figure 19:
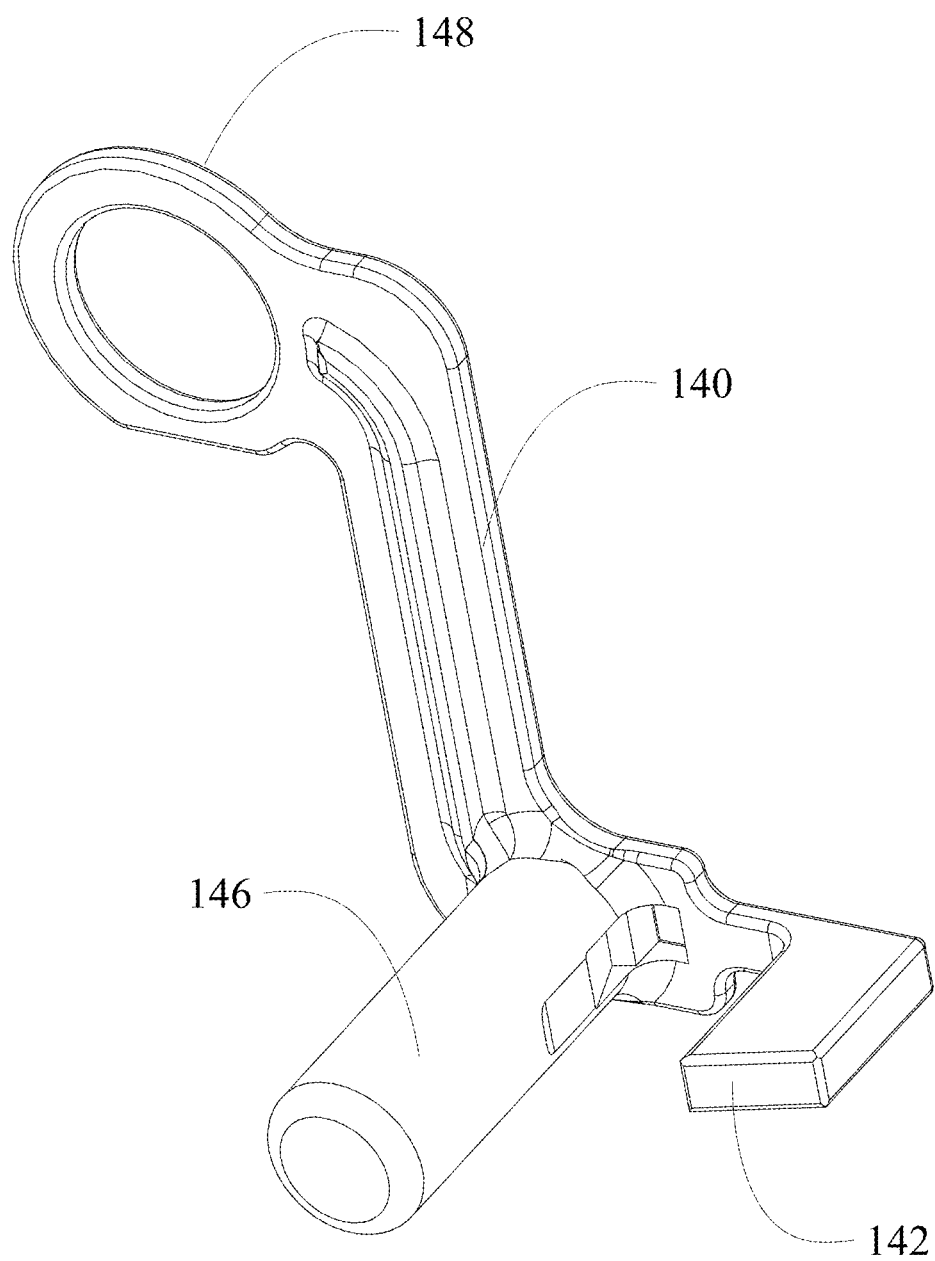
FIG. 19 is an isometric view of the floating arm.

Returning to FIG. 1, an alternative strap tensioning system is provided for the upper strap 120 on the lower attachment assembly 14. This strap 120 differs from the other straps on the brace in that it encircles the calf as opposed to originating on a lateral support and terminating on a medial support after passing posterior to the leg. A single point tensioning assembly 122 is provided with ratcheting tensioning and a single point attachment and release system as shown in FIGS. 16-21B. Strap 120 extends from the single point tensioning assembly 122 traversing the posterior of the calf and extending through a guide 124 on the medial support 22 in the lower attachment assembly 14 (as best seen in FIG. 1). The strap 120 then passes anterior to the calf just below the knee and attaches to the single point tensioning system 122. As shown in FIGS. 16, 17 and 18, strap 120 (shown in phantom) terminates in a bullnose 126 which is received in a connection channel 128 (the front of the connection channel is not shown for clarity of the remaining elements) on the single point tensioning assembly 122. A knob 130 is turned for tensioning the strap as will be described in greater detail subsequently. A gear assembly 132 employs a drive gear 134a on a spindle 136 extending from the knob 130 to drive a bevel gear 134b attached to a spring loaded spool 138 to retract and extend the strap 120. A single point release having a floating arm 140 is integrated in the single point tensioning system 122. The floating arm 140, shown in detail in FIG. 15, includes a lock tooth 142 which is received in an engagement slot 144 in the bullnose 126 to constrain the bullnose in the connection channel 128 (best seen in FIGS. 16 and 18). A release button 146 extends from the floating arm for single point release actuation and strap retraction as will be described subsequently. A ratchet release hoop 148 is rigidly attached to the floating arm to release the tensioning ratchet as will be described in greater detail subsequently.

Figure 20A:
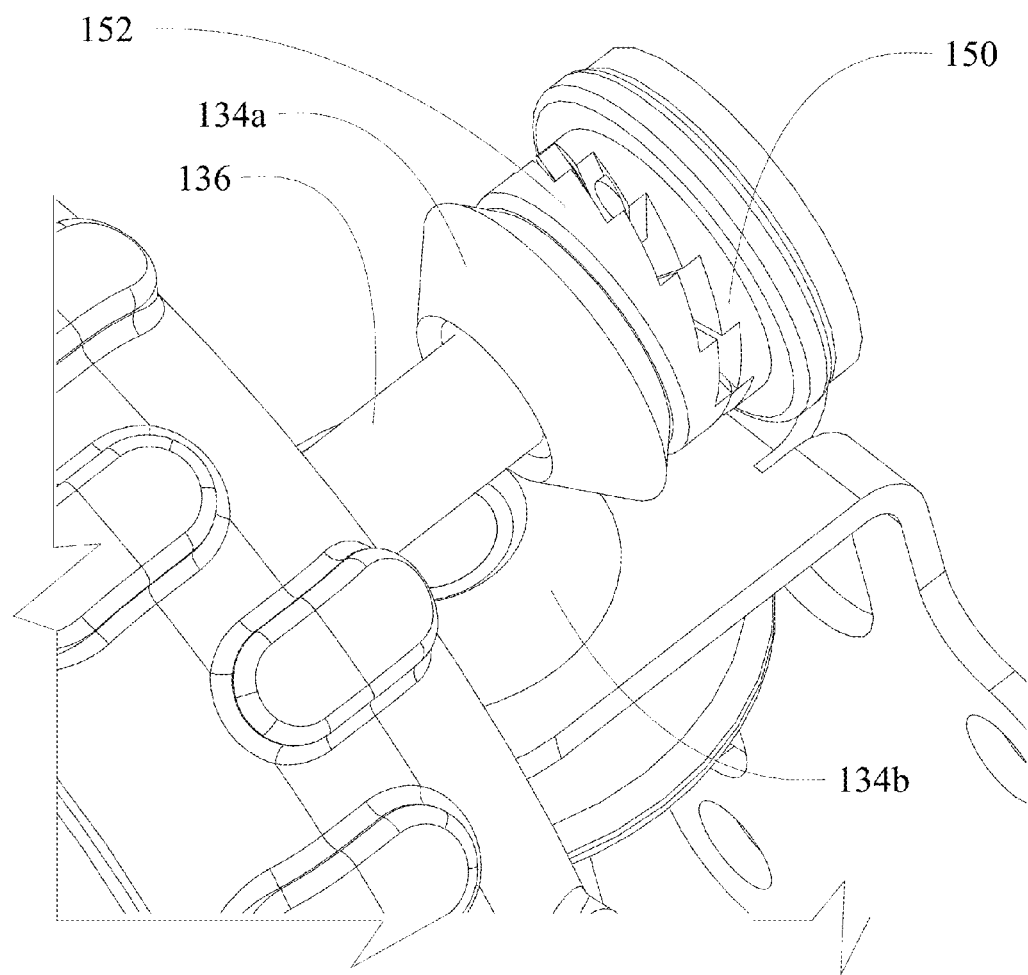
FIG. 20A is an isometric view of the ratchet and ratchet stop in the disengaged position without the floating arm ratchet release loop for clarity.
Figure 20B:
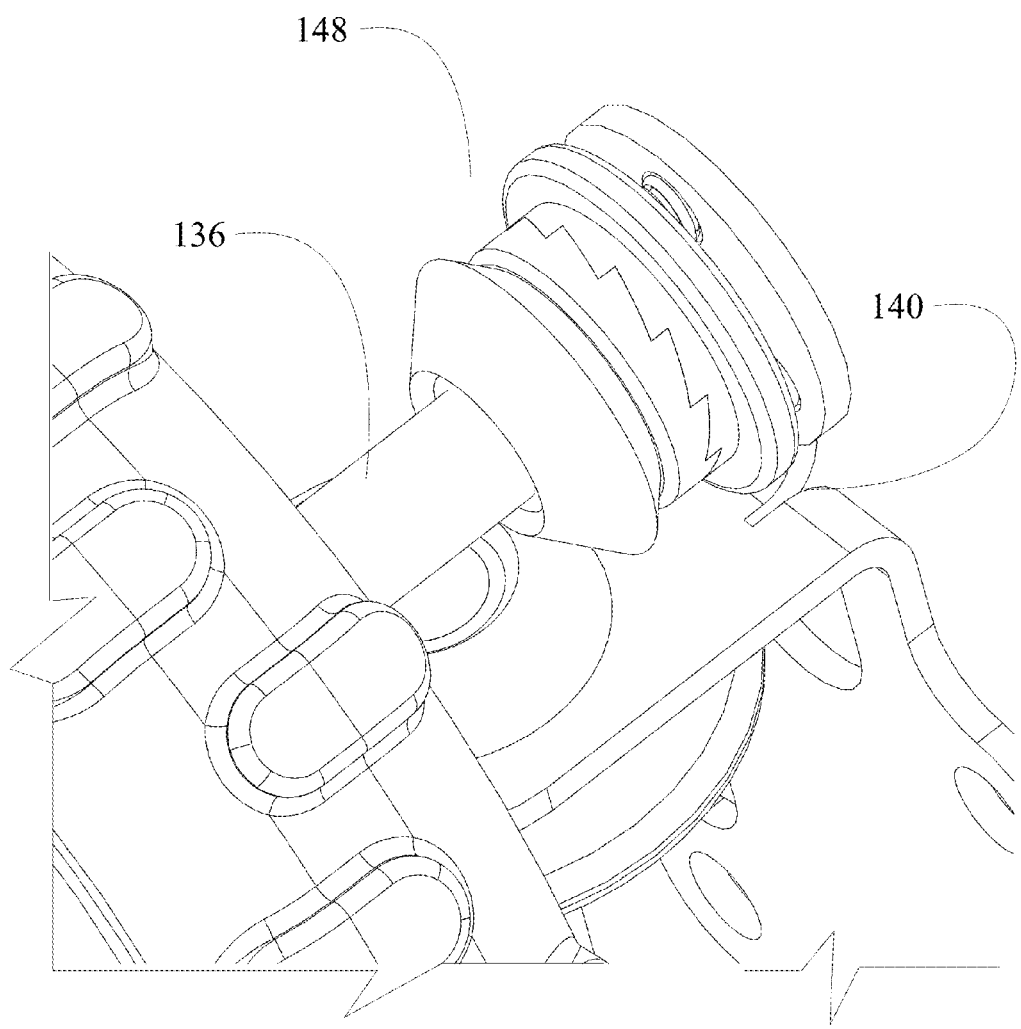
FIG. 20B is an isometric view of the ratchet and ratchet stop in the engaged position without the floating arm ratchet release loop for clarity.
Figure 20C:
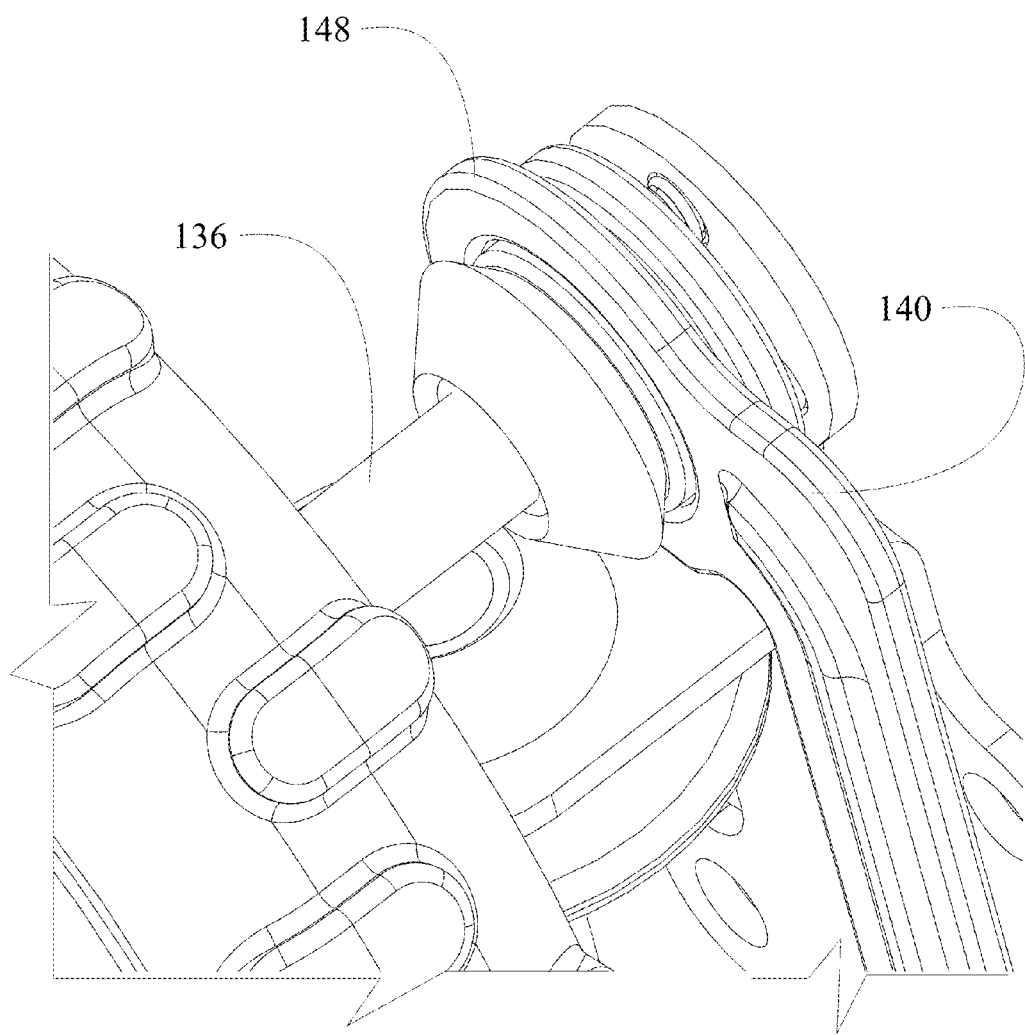
FIG. 20C is an isometric view with the ratchet release loop shown.
Figure 21A:
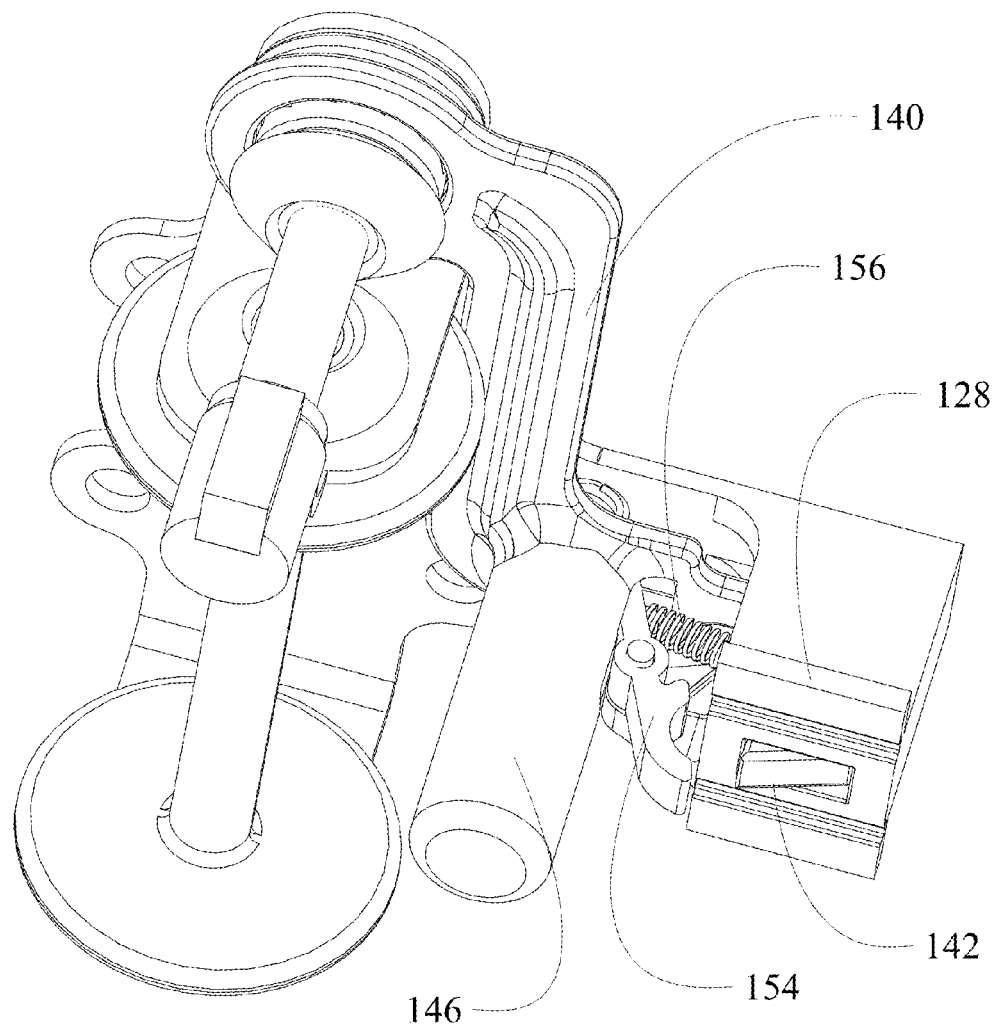
FIG. 21A is an isometric detail view prior to insertion of the bullnose of the center pivot lever arm engaged to restrain the floating arm in the first position.
Figure 21B:
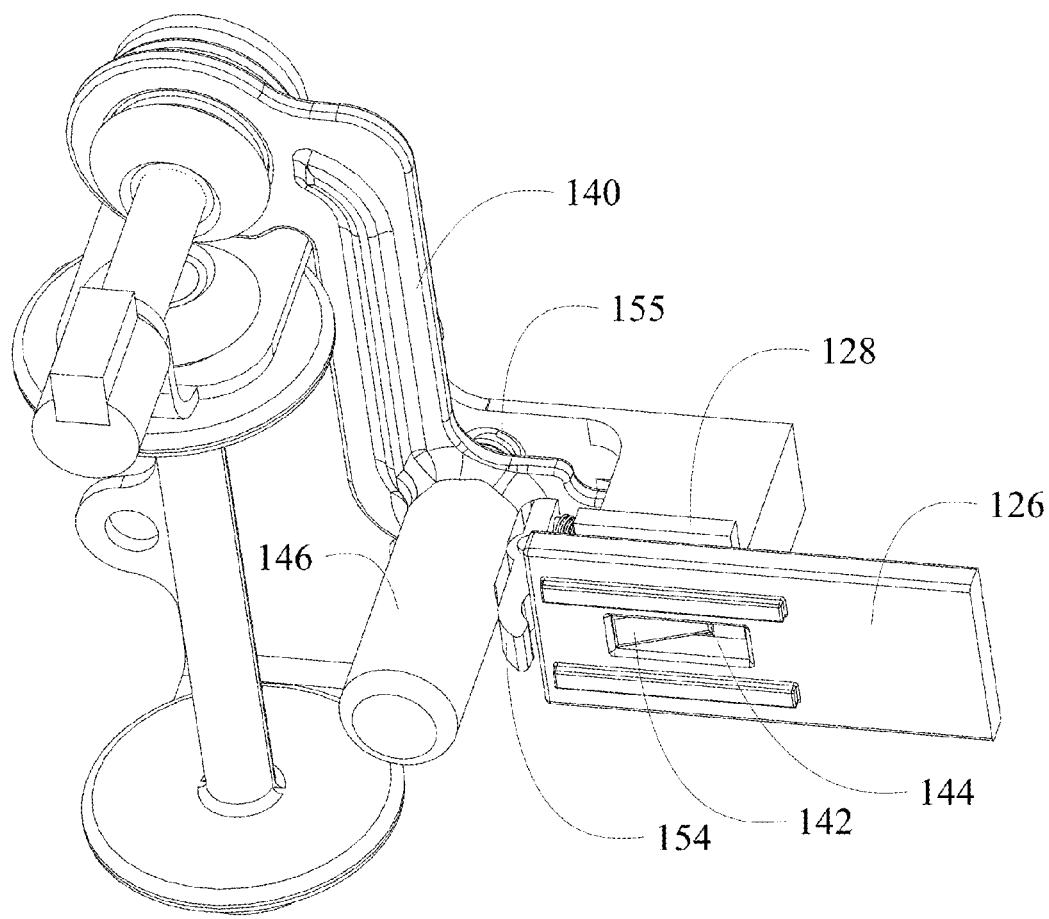
FIG. 21B is an isometric detail view of the center pivot lever arm after insertion of the bullnose with the floating arm released to the second position.

Operation of the single point tensioning assembly 122 is best understood with regard to FIGS. 20A-20C and 21A, 21B. As shown in FIG. 20A, in an initial state the floating arm 140 is held, as will be described in greater detail subsequently, in a first position which causes the ratchet release hoop 148 (shown in FIG. 20C but not shown in FIG. 20A for clarity) to disengage a ratchet stop 150, which is spring biased along the axis of the spindle 136, from a ratchet wheel 152 attached to the spindle behind drive gear 134a. In this condition, the spring loaded spool 138 is tensioned to retract the strap 120 or allow extension of the strap winding the spool against its spring. The user extends the strap from the spool 138 around the posterior of the calf, through the guide 124 on the medial support 22 and inserts the bullnose 126 into the connection channel 128. Prior to insertion of the bullnose into the connection channel, a center pivot lever 154 rests in a lock position, urged by a spring 156 as shown in FIG. 21A, restraining the floating arm 140 in the first position. Upon insertion of the bullnose 126 into the connection channel 128 as shown in FIG. 21B, the bullnose engages and causes the center pivot lever 154 to pivot to a second position compressing spring 156 and releasing the floating arm 140 which is urged by spring 158 into a second position engaging the tooth 142 into the slot 144 in the bullnose to constrain the bullnose in the connection channel and repositioning the ratchet release hoop 148 to release the ratchet stop 150 allowing it to engage the ratchet wheel 152 as shown in FIG. 20B. In this configuration, the knob 130 may be rotated clockwise to rotate the spool 138 through gear assembly 132 to tension the strap 120 as desired. Ratchet stop 150 urged axially along the spindle by springs 151 engages the ratchet wheel 152 to maintain tension.

To remove the brace, strap 120 is released by depressing the release button 146, which by depressing the floating arm against spring 158 back to the first position simultaneously disconnects the bullnose 126 from the connection channel 128 by retracting the connected lock tooth 142 from slot 144 and releases the ratchet stop 150 with the release loop 148. Center pivot lever 154, released by removal of the bullnose, is urged by spring 156 into the lock position constraining the floating arm 140 in the first position for free rotation of the ratchet wheel 152, gear assembly 132 and spool 138 to retract the strap 120.

While described as a clockwise tightening system for typical right handed operation, the elements of the single point tensioning assembly 122 may be fabricated in mirror image to operate in a counterclockwise tightening system for left handed operation.

While described herein as a unitary assembly on a knee brace embodiment, the cinching system assemblies and single point tensioning assembly with their associated strapping may be employed separately on various orthopedic braces or other devices for strap tensioning.

Figure 22:
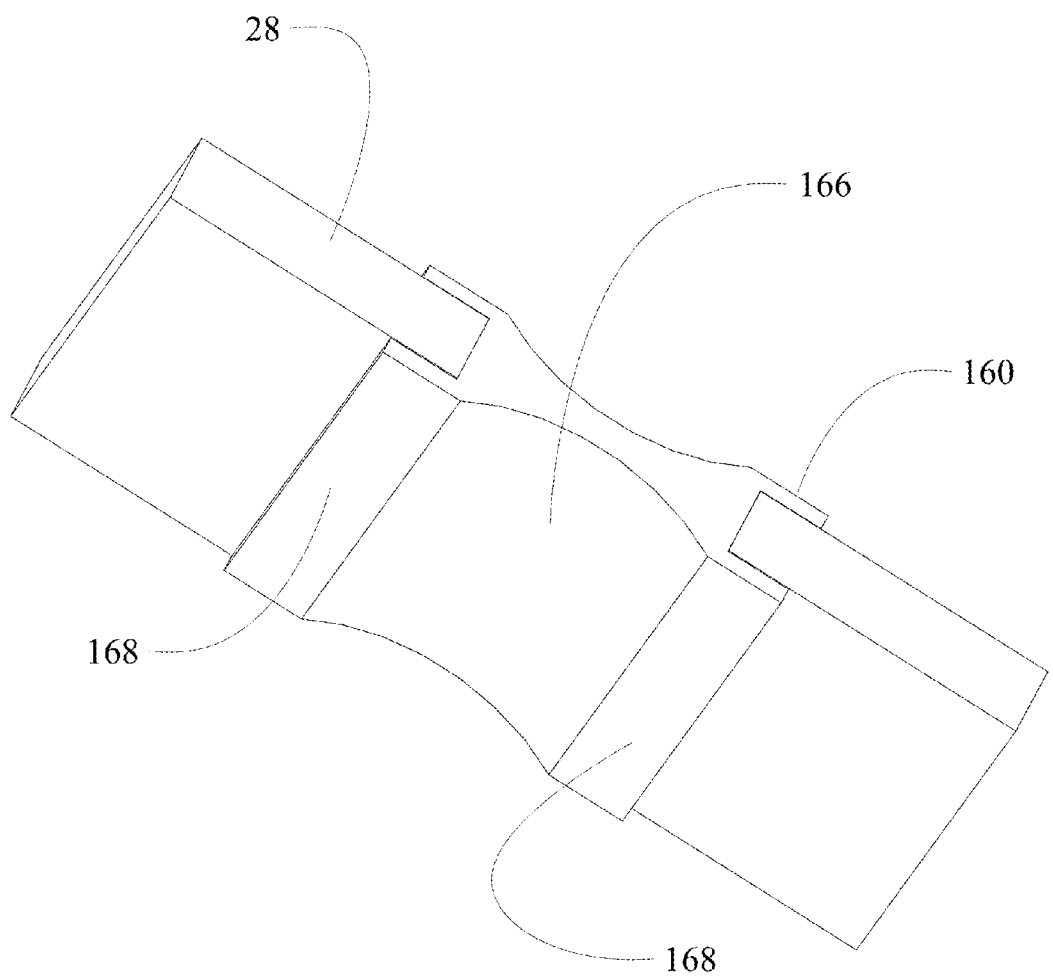
FIG. 22 is an isometric detail view of an embodiment of a living hinge embodiment for the lateral relief hinge of FIGS. 1A and 2B; and, FIGS. 23A and 23B are simplified front and side views of the knee brace demonstrating orientation and operation of the lateral relief hinge.
Figure 23A:
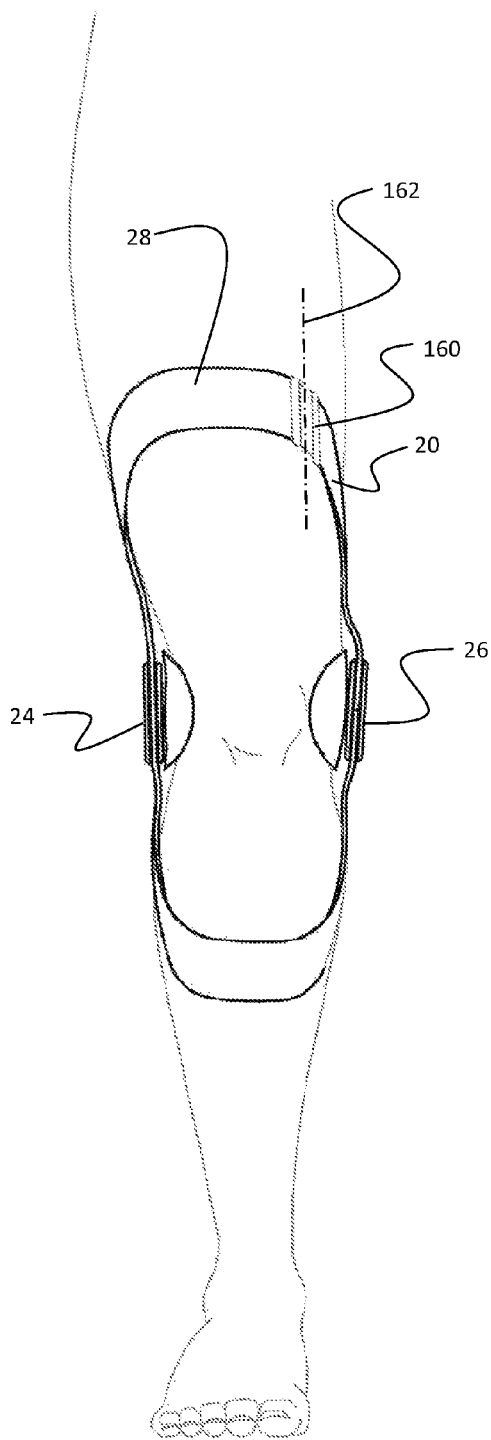
Figure 23B:
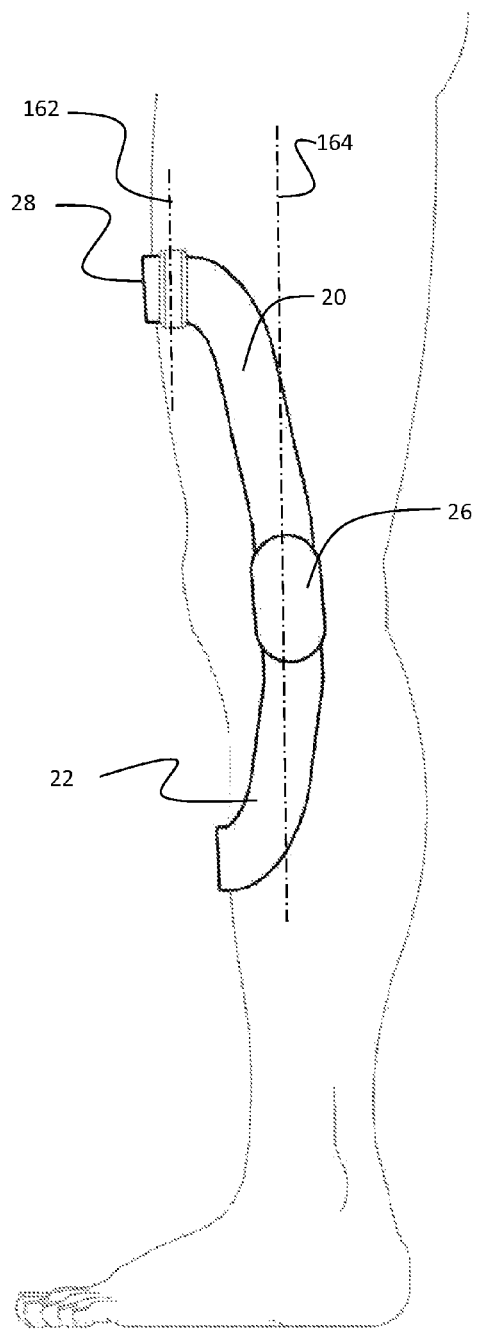

The knee brace additionally incorporates a lateral flex feature to allow non-parallel alignment of the side hinges 24 and 26 on the knee brace 10 without binding during flexing of the knee. A hinge element 160 is integral to the anterior arch support 28 seen in FIGS. 2A and 2B and shown in detail in FIGS. 22, 23A and 23B. The hinge element 160 is located in the anterior arch support 28 substantially at the intersection of the anterior arch support and the medial support 20. An axis 162 of the hinge element 160 is substantially perpendicular to an axis of rotation of the medial hinge 26 and substantially parallel to a neutral axis 164 of the leg, medial support 20, and lower medial support 22 with the knee in the normal unflexed position. The hinge element 160 is sufficiently flexible to allow a medially inward angular offset of the medial support 20 of up to 6° from a neutral position with the leg and brace unflexed to a flexed position. This feature allows the medial hinge 26 to operate without binding without requiring that the axes of rotation of the medial and lateral hinge be aligned. The hinge element 160 may be a living hinge as shown in FIG. 22 with a reduced thickness portion 166 of material more flexible than the attachment portions 168 engaging the anterior arch support 28. A conventional hinge, such as a piano hinge, may alternatively be employed or a molded thinning of the material of the anterior arch support 28 at the desired hinge element location.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:
1. A cinching system for a strap comprising:
a knob rotatable in a first direction about an axis of rotation;
an engagement element interconnected to the knob for rotation by the knob in the first direction;
a gear assembly rotatable by the engagement element;
a shaft engaging the gear assembly for rotation, said gear assembly centrally located on the shaft, said shaft oriented orthogonal to the axis of rotation of the knob and having opposing ends extending from the gear assembly; and, a strap having two parallel bands engaged on the opposing ends of the shaft and extendible from the shaft and retractable on the shaft upon rotation of the shaft by the gear assembly.

2. The cinching system as defined in claim 1 further comprising:
a coil spring carried on the shaft for retraction of the strap.

3. A cinching system for a strap comprising:
a knob rotatable in a first direction about an axis of rotation;
an engagement element interconnected to the knob for rotation by the knob in the first direction wherein the engagement element comprises:
at least one cinching plate engaged by the knob for rotation in the first direction in a first orientation and transitioning to a second orientation upon rotation of the knob in a second direction,
a ratchet wheel engaged by the at least one cinching plate in the first orientation for rotation in the first direction, and
at least one ratchet arm engaging the ratchet wheel for ratcheting operation and engaged by the at least one cinching plate in the second orientation for disengagement from the at least one ratchet arm,
a gear assembly rotated in response to rotation of the ratchet wheel;
a shaft engaging the gear assembly for rotation, said shaft oriented orthogonal to the axis of rotation of the knob; and
a strap extendible from the shaft and retractable on the shaft upon rotation of the shaft by the gear assembly.

4. A cinching system for a strap comprising:
a knob rotatable in a first direction about an axis of rotation;
an engagement element interconnected to the knob for rotation by the knob in the first direction, wherein the engagement element comprises:
a first tooth ring depending from the knob;
a second tooth ring engaging the first tooth ring positionable between an elevated position and a depressed position, said second tooth ring having an oppositely oriented tooth set; and,
a third tooth ring engaging the oppositely oriented tooth set in the elevated position and disengaged from the first tooth ring in the depressed position, said third tooth ring operably attached to a gear assembly;
a shaft engaging the gear assembly for rotation, said shaft oriented orthogonal to the axis of rotation of the knob; and
a strap extendible from the shaft and retractable on the shaft upon rotation of the shaft by the gear assembly.

5. The cinching system as defined in claim 4 further comprising:
at least one ratchet pawl engaging a ratchet ring extending from the knob, engagement of said ratchet ring by the at least one ratchet pawl preventing rotation in a direction opposite the first direction.

6. The cinching system as defined in claim 4 further comprising:
a resilient retention element engaging the second tooth ring in the depressed position; and,
a ramp engaging the second tooth ring, said ramp urging the second tooth ring to disengage from the resilient retention element into the elevated position upon rotation of the knob in the first direction.

7. A tensioning assembly for orthopedic braces comprising:

a knob having a spindle with an attached ratchet;
a spool engaged for rotation by the spindle;
a floating arm having a first position and a second position, said floating arm including
a locking tooth extendible into a connection channel in the second position,
a ratchet release loop positioning a ratchet lock for engagement of the ratchet in the second position;
a release button for moving the floating arm from the second position to the first position;
a strap having a bullnose removably receivable in the connection channel, said bullnose having a slot to receive the locking tooth and releasing the floating arm from said first position to said second position upon insertion into the connection channel, said strap extendible from and retractable on the spool.

8. The tensioning assembly for orthopedic braces as defined in claim 7 further comprising:
a pivoting lever locking the floating arm in the first position, said lever pivoting upon engagement by the bullnose to release the floating arm to the second position.

9. A knee brace comprising:
an anterior arch support;
a medial support extending from the anterior arch support;
a medial hinge attached to the medial support distal the anterior arch support;
a relief hinge integrated in the anterior arch support proximate the medial support, said relief hinge having an axis of rotation substantially perpendicular to an axis of rotation of the medial hinge and substantially parallel to an unflexed neutral axis on the medial support extending through the medial hinge.

10. The knee brace as defined in claim 9 further comprising:
at least one cinching system extending between the medial support and a lateral support, said at least one cinching system having
a knob mounted to the lateral support and rotatable in a first direction about an axis of rotation;
an engagement element interconnected to the knob for rotation by the knob in the first direction;
a gear assembly rotatable by the engagement element;
a shaft engaging the gear assembly for rotation, said shaft oriented orthogonal to the axis of rotation of the knob; and,
a strap extendible from the shaft and retractable on the shaft upon rotation of the shaft by the gear assembly.

11. The knee brace as defined in claim 10 wherein the engagement element comprises:
a first tooth ring depending from the knob;
a second tooth ring engaging the first tooth ring positionable between an elevated position and a depressed position, said second tooth ring having an oppositely oriented tooth set; and,
a third tooth ring engaging the oppositely oriented tooth set in the elevated position and disengaged from the first tooth ring in the depressed position, said third tooth ring operably attached to the gear assembly.

12. The knee brace as defined in claim 11 further comprising:
at least one ratchet pall engaging a ratchet ring extending from the knob, engagement of said ratchet ring by the at least one ratchet pall preventing rotation in a direction opposite the first direction.

13. The knee brace as defined in claim 11 further comprising:

a resilient retention element engaging the second tooth ring in the depressed position; and, a ramp engaging the second tooth ring, said ramp urging the second tooth ring to disengage from the resilient retention element into the elevated position upon rotation of the knob in the first direction.

14. The knee brace as defined in claim 10 further comprising:

a coil spring carried on the shaft for retraction of the strap.

* * * * *